United States Patent
Naber et al.

(10) Patent No.: US 7,241,468 B2
(45) Date of Patent: Jul. 10, 2007

(54) REDUCED CALORIE FAT COMPOSITIONS

(75) Inventors: Russell Bruce Naber, Cincinnati, OH (US); Jeffrey John Kester, West Chester, OH (US); Johnson Watson McRorie, Jr., Lebanon, OH (US); Stacey Lynne Adams, Ft. Collins, OH (US); Richard Gerard Schafermeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 536 days.

(21) Appl. No.: 10/149,875

(22) PCT Filed: Dec. 18, 2000

(86) PCT No.: PCT/US00/34387

§ 371 (c)(1),
(2), (4) Date: Oct. 11, 2002

(87) PCT Pub. No.: WO01/43558

PCT Pub. Date: Jun. 21, 2001

(65) Prior Publication Data

US 2003/0215556 A1    Nov. 20, 2003

Related U.S. Application Data

(60) Provisional application No. 60/172,507, filed on Dec. 17, 1999.

(51) Int. Cl.
A23D 9/007    (2006.01)
(52) U.S. Cl. .................. 426/611; 426/612; 426/804
(58) Field of Classification Search ............... 426/611, 426/612, 804
See application file for complete search history.

(56) References Cited

U.S. PATENT DOCUMENTS

| | | | |
|---|---|---|---|
| 2,831,854 A | 4/1958 | Tucker et al. | |
| 2,962,419 A | 11/1960 | Minich | |
| 3,579,548 A | 5/1971 | Whyte | |
| 3,600,186 A | 8/1971 | Mattson et al. | |
| 3,932,532 A | 1/1976 | Hunter et al. | |
| 3,963,699 A | 6/1976 | Rizzi et al. | |
| 4,005,195 A | 1/1977 | Jandacek | |
| 4,005,196 A | 1/1977 | Jandacek et al. | |
| 4,034,083 A | 7/1977 | Mattson | |
| 4,455,333 A | 6/1984 | Hong et al. | |
| 4,508,746 A | 4/1985 | Hamm | |
| 4,517,360 A | 5/1985 | Volpenhein | |
| 4,518,772 A | 5/1985 | Volpenhein | |
| 4,582,927 A | 4/1986 | Fulcher | |
| 4,840,815 A | 6/1989 | Meyer et al. | |
| 4,861,613 A | 8/1989 | White et al. | |
| 4,888,195 A | 12/1989 | Huhn et al. | |
| 4,983,329 A | 1/1991 | Cooper | |
| 5,071,669 A * | 12/1991 | Seiden | 426/660 |
| 5,175,323 A | 12/1992 | Cooper | |
| 5,273,772 A | 12/1993 | Cooper | |
| 5,288,512 A | 2/1994 | Seiden | |
| 5,288,884 A | 2/1994 | Cooper | |
| 5,298,637 A | 3/1994 | Cooper | |
| 5,304,665 A | 4/1994 | Cooper et al. | |
| 5,306,514 A | 4/1994 | Letton et al. | |
| 5,306,515 A | 4/1994 | Letton et al. | |
| 5,306,516 A | 4/1994 | Letton et al. | |
| 5,362,894 A | 11/1994 | Handwerker et al. | |
| 5,374,446 A | 12/1994 | Ferenz et al. | |
| 5,387,429 A | 2/1995 | Cooper | |
| 5,399,728 A | 3/1995 | Cooper | |
| 5,399,729 A | 3/1995 | Cooper et al. | |
| 5,419,925 A | 5/1995 | Seiden et al. | |
| 5,427,815 A | 6/1995 | Ferenz | |
| 5,446,843 A | 8/1995 | Fucito et al. | |
| 5,451,416 A * | 9/1995 | Johnston et al. | 426/531 |
| 5,480,667 A * | 1/1996 | Corrigan et al. | 426/531 |
| 5,490,995 A * | 2/1996 | Corrigan | 426/531 |
| 5,492,714 A * | 2/1996 | Guskey et al. | 426/607 |
| 5,512,313 A | 4/1996 | Cooper et al. | |
| 5,516,544 A | 5/1996 | Sekula et al. | |
| 5,534,284 A * | 7/1996 | Corrigan et al. | 426/531 |
| 5,589,217 A | 12/1996 | Mazurek | |
| 5,597,605 A | 1/1997 | Mazurek | |
| 5,603,978 A | 2/1997 | White et al. | |
| 6,261,628 B1 * | 7/2001 | Howie | 426/611 |
| 6,562,394 B1 * | 5/2003 | Volker | 426/606 |

FOREIGN PATENT DOCUMENTS

| | | |
|---|---|---|
| EP | 0 236 288 | 9/1987 |
| EP | 0 325 010 B1 | 3/1993 |
| WO | WO 97/22260 | 6/1997 |

OTHER PUBLICATIONS

Hamilton, et al.—"Fats and Oils: Chemistry and Technology", Applied Science Publishers, Ltd., London (1980), pp. 93-96.
Swern—"Bailey's Industrial Oil and Fat Products", 3rd Ed. (1964), pp. 941-943 and 958-965.
Applewhite—"Bailey's Industrial Oil and Fat Products",vol. 3, 4th Ed. (1985), pp. 1-39.
Madison, et al.—Journal of the American Oil Chem. Society, vol. 55 (1978), pp. 328-331.

* cited by examiner

Primary Examiner—Carolyn Paden
(74) Attorney, Agent, or Firm—S. Robert Chuey; Carl J. Roof

(57) ABSTRACT

Reduced calorie fat compositions which contain combinations of substantially non-absorbable, substantially nondigestible polyol polyesters and certain reduced calorie triglycerides that function as anti-anal leakage agents and provide textural/taste benefits are disclosed. These reduced calorie fat compositions are useful in a variety of food applications, including frying oils for salted snacks, chocolate-flavored candy bars and cooking/salad oils.

4 Claims, No Drawings

US 7,241,468 B2

REDUCED CALORIE FAT COMPOSITIONS

CROSS-REFERENCE TO RELATED APPLICATIONS

This application is a 371 of PCT/US00/34387, file Dec. 18, 2000, which claims the benefit of U.S. Provisional Application No. 60/172,507, filed Dec. 17, 1999.

BACKGROUND OF THE INVENTION

The present application relates to reduced calorie fat compositions which contain combinations of non-absorbable, nondigestible polyol polyesters and reduced calorie triglycerides that function as anti-anal leakage agents and provide textural/taste benefits, e.g., less waxiness/greasiness, improved mouthmelt. The present application further relates to food products, such as frying oils for salted snacks, firm chocolate-flavored products and cooking/salad oils, containing combinations of these polyesters and triglycerides.

Polyol fatty acid polyesters are known in the art for use as low calorie substitutes for normal triglyceride fats. For example, U.S. Pat. No. 3,600,186 to Mattson et al., issued Aug. 17, 1971, discloses low calorie food compositions in which at least a portion of the fat content of a conventional food is provided by a non-absorbable, nondigestible sugar fatty acid polyester with each fatty acid having from 8 to 22 carbon atoms. Foods in which these polyol polyesters are particularly useful include salad and cooking oils, mayonnaise, margarine, dairy products, and plastic shortenings for use in frying, cake making, breadmaking or the like.

Unfortunately, regular ingestion of moderate to high levels of liquid forms of these polyol polyesters can produce an undesirable laxative side effect, namely, leakage of the polyesters through the anal sphincter. U.S. Pat. No. 4,005,195 to Jandacek, issued Jan. 25, 1977 discloses a means for preventing these undesirable laxative effects through the addition of anti-anal leakage agents. These anti-anal leakage agents include solid fatty acids (melting point 37° C. or higher) and their digestible triglyceride and ester sources, as well as edible solid, nondigestible, non-absorbable polyol fatty acid polyesters. Solid fatty acids, solid triglycerides and solid polyol polyesters have drawbacks when used as anti-anal leakage agents in low calorie food compositions. For example, a fatty acid, triglyceride or polyester providing a high solids content at body temperature tastes waxy in the mouth when ingested. Additionally, cooking and salad oils containing solid fatty acids, solid triglycerides or solid polyol polyesters can be cloudy or opaque at room temperature, i.e., at about 70° F. (21.1° C.), or below, instead of clear. Accordingly, it would be desirable to provide anti-anal leakage agents for liquid polyol polyesters which do not impart a waxy mouthfeel and can be used in formulating clear cooking oils.

U.S. Pat. No. 4,005,196 to Jandecek et al., issued Jan. 25, 1977, discloses the combination of liquid polyol polyesters, anti-anal leakage agents, and fat soluble vitamins selected from vitamin A, vitamin D, vitamin E and vitamin K.

SUMMARY OF THE INVENTION

The present invention relates to reduced calorie fat compositions, which comprise:
a. from about 65% to about 85% of an edible, substantially non-absorbable, substantially nondigestible polyol fatty acid polyester comprising <3% solids at body temperature (98.6° F., 37° C. ), preferably 0% solids at body temperature, (i.e. which has a melting point less than or equal to 37° C.), having at least 2, preferably having at least 4 fatty acid ester groups; preferably wherein the polyol is selected from sugars and sugar alcohols containing from 4 to 8 hydroxyl groups; and wherein each fatty acid group has from 2 to 24 carbon atoms; and
b. from about 15% to about 35% reduced calorie triglycerides selected from MMM, MLM, MML, LLM, LML and LLL triglycerides, and mixtures thereof; wherein M is a saturated fatty acid residue selected from $C_6$ to $C_{10}$ saturated fatty acids, and mixtures thereof; wherein L is a saturated fatty acid residue selected from $C_{18}$ to $C_{24}$ saturated fatty acids and mixtures thereof; wherein the reduced calorie triglycerides comprise: (1) at least about 85%, preferably at least about 90% combined MLM, MML, LLM and LML triglycerides; (2) up to about 15%, preferably up to about 10%, combined MMM and LLL triglycerides, and wherein the fatty acid composition of the reduced calorie triglycerides comprises: (1) from about 10% to about 70%, preferably from about 20% to about 65% $C_6$ to $C_{10}$ saturated fatty acids; (2) from about 30% to about 90%, preferably from about 40% to about 80% $C_{18}$ to $C_{24}$ saturated fatty acids; and (3) from about 20% to about 80%, preferably from about 30% to about 70% $C_{20}$ to $C\ 24$ saturated fatty acids.

Additionally, the present invention relates to reduced calorie fat compositions, which comprise:
a. from about 10% to about 85% of an edible, substantially non-absorbable, substantially non-digestible polyol fatty acid polyester which comprises at least 3% of a solid non-digestible polyol polyester component having a melting point of greater than 37° C. (i.e. ≧3% solids at body temperature), having at least 2, preferably at least 4, fatty acid ester groups; wherein the polyol is preferably selected from sugars and sugar alcohols containing from 4 to 8 hydroxyl groups; and wherein each fatty acid group has from 2 to 24 carbon atoms; and
b. from about 15% to about 90% reduced calorie triglycerides selected from MMM, MLM, MML, LLM, LML and LLL triglycerides, and mixtures thereof; wherein M is a saturated fatty acid residue selected from $C\ 6$ to $C\ 10$ saturated fatty acids, and mixtures thereof; wherein L is a saturated fatty acid residue selected from $C_{18}$ to $C\ 24$ saturated fatty acids, and mixtures thereof; wherein the reduced calorie triglycerides comprise: (1) at least about 85% combined MLM, MML, LLM and LML triglycerides; (2) up to about 15% combined MMM and LLL triglycerides, and wherein the fatty acid composition of the reduced calorie triglycerides comprises: (1) from about 10% to about 70% $C\ 6$ to $C\ 10$ saturated fatty acids; (2) from about 30% to about 90% $C_{18}$ to $C_{24}$ saturated fatty acids; and (3) from about 20% to about 80% $C20$ to $C_{24}$ saturated fatty acids.

Additionally, the present invention relates to reduced calorie fat compositions, which comprise:
a. from about 10% to about 95% of an edible, substantially non-absorbable, substantially nondigestible polyol fatty acid polyester which comprises at least 3% of a solid non-digestible component which is a high $C_{20}$ and above long-chain fatty acid polyol polyester having a melting point of greater than 37° C.; having at least 2, preferably at least 4, fatty acid ester groups; wherein the polyol is preferably selected from sugars and sugar alcohols containing from 4 to 8 hydroxyl groups; and wherein each fatty acid group has from 2 to 24 carbon atoms; and b. from about 5% to about 90% reduced calorie triglycerides selected from MMM, MLM, MML, LLM, LML and LLL triglycerides, and mixtures thereof; wherein M is a saturated fatty acid residue selected from C 6 to C 10 saturated fatty acids, and mixtures thereof; wherein L is a saturated fatty acid residue selected from $C_{18}$ to C 24 saturated fatty acids, and mixtures thereof; wherein the reduced calorie triglycerides comprise: (1) at least about 85% combined MLM, MML, LLM and LML triglycerides; (2) up to about 15% combined MMM and LLL triglycerides, and wherein the fatty acid composition of the reduced calorie triglycerides comprises: (1) from about 10% to about 70% C 6 to C 10 saturated fatty acids; (2) from about 30% to about 90% $C_{18}$ to $C_{24}$ saturated fatty acids; and (3) from about 20% to about 80% C20 to $C_{24}$ saturated fatty acids.

The present invention further relates to food products which comprise these reduced calorie fat compositions as the sole ingredient, or in combination with other fat ingredients such as triglyceride oils. These food products include frying oils for salted snacks, margarines and other fried foods, firm chocolate-flavored products such as chocolate-flavored candy bars or chips, solid and opaque fluid shortenings, peanut butters and spreads, as well as cooking and salad oils that are clear at room temperature, i.e., about 70° F. (21.1° C.), and preferably at lower temperatures, e.g., at about 50° F. (10° C.). Surprisingly, the reduced calorie triglycerides function as anti-anal leakage agents for the polyol polyesters. In addition, the combination of the polyol polyesters with the reduced calorie triglycerides provides significant advantages over the use of either component alone. The advantages provided by these combinations include: (1) increased caloric reduction; (2) textural/taste benefits (e.g., less waxiness/greasiness, improved mouth-melt); (3) less oxidative degradation during frying; and (4) less high temperature volatility and foaming during frying.

When liquid (melting point <37° C.) polyol polyesters are used, it has been found that at least about 15% reduced calorie triglycerides must be used in combination with the liquid polyol polyester to have acceptable oil-loss control. The minimum of 15% reduced calorie triglycerides is thought to change the stool rheology of subjects who ingest the reduced calorie fat compositions of the present invention so that there is a tendency towards stiffer stools. While not intending to be bound by theory, it is believed that, by incorporating at least 15% reduced calorie triglycerides in the reduced calorie fat compositions of the present invention, there is increased control of oil separation from the fecal matrix, and that, by reducing oil separation, there is a lower probability of oil leakage through the anal sphincter.

Additionally, if the non-digestible polyol polyester component of the present invention incorporates at least 3% solid polyol polyester (i.e., has a melting point of greater than 37° C.) which, is a high $C_{20}$ and where long-chain fatty acid polyol polyester, then as little as about 5% of the reduced calorie triglycerides can be used in the reduced calorie fat composition of the present invention.

DETAILED DESCRIPTION OF THE INVENTION

A. Definitions

By "substantially nondigestible, substantially non-absorbable" as used herein is meant a polyol polyester which is about 30% or less digested and absorbed. Preferred polyesters are about 10% or less digested and absorbed.

By "reduced calorie triglycerides" as used herein is meant triglycerides that provide an at least about 10%, and preferably an at least about 30%, reduction in calories relative to corn oil. These reduced calorie triglycerides usually provide between about 20% and about 50% reduction in calories. The reduction in calories provided by the present reduced calorie triglycerides is based on the net energy gain (in Kcal) of rats that have ingested a diet containing a fat consisting of the reduced calorie triglycerides, relative to the net energy gain (in Kcal) of rats that have ingested an identical diet, but containing corn oil instead of the fat consisting of the reduced calorie triglycerides. The test diets used are nutritionally adequate to support both maintenance and growth of the rats. Total food intake and fat/oil intake are also matched between the two diet groups so that differences in net carcass energy gain are due entirely to the utilizable energy content of the fat/oil. "Net energy gain" is based on the total carcass energy (in Kcal) of the rats fed the test diet for some period of time (usually 4 weeks), reduced by the mean starting carcass energy (in Kcal) determined from a study of a different group of rats of the same sex, strain, and similar body weight fed a test diet that does not contain the fat/oil. "Total carcass energy" is determined by the dry carcass energy per gram (Kcal per gram) multiplied by the dry weight of the carcass (in grams). "Carcass energy per gram" is based on the carcass energy (in Kcal) as determined by bomb calorimetry of a homogeneous sample of the total dry carcass. All of these energy values are the average of a representative sample of rats (i.e., 10 rats).

By "medium chain saturated fatty acids," as used herein, is meant $C_{6:0}$ (caproic), $C_{8:0}$ (caprylic), or $C_{10}$:0 (capric) fatty acids, or mixtures thereof. The C7 and C9 saturated fatty acids are not commonly found, but they are not excluded from the possible medium chain fatty acids. The present medium chain fatty acids do not include lauric acid (C12:0), sometimes referred to in the art as a medium chain fatty acid. The term "high $C_{20}$ and above long-chain fatty acid polyol polyesters" includes solid polyol polyesters which comprise novel solid polyol polyesters wherein the polyol has at least 4 hydroxyl groups, the ester groups comprise a combination of: (I) long chain (at least 12 carbon atoms) unsaturated fatty acid radicals, or a mixture of said radicals and saturated short chain ($C_2$–$C_{12}$) fatty acid radicals, and (ii) long chain (at least 20 carbon atoms) saturated fatty acid radicals, in a molar ratio of I:II of from about 1:15 to about 2:1, and wherein at least 4 of the hydroxyl groups of the polyol are esterified.

By "long chain saturated fatty acids," as used herein, is meant, $C_{18:0}$ (stearic), C19:0 (nonadecylic), C20:0 (arachidic), C21:0 (heneicosanoic), C22:0 (behenic), C23:0 (tricosanoic), or $C_{24:0}$ (lignoceric), or mixtures thereof.

In the above listing of fatty acid moieties, the common name of the fatty acid is given following its Cx:y designation (wherein x is the number of carbon atoms, and y is the number of double bonds).

By "MML," as used herein, is meant a triglyceride containing a long chain saturated fatty acid residue in the #1 or #3 position (an end position) with two medium chain saturated fatty acid residues in the remaining two positions.

(The absorption of long chain saturated fatty acids is generally reduced in the end positions.) Similarly, "MLM" represents a triglyceride with a long chain saturated fatty acid residue in the #2 position (the middle position) and two medium chain fatty acid residues in the #1 and #3 positions, "LLM" represents a triglyceride with a medium chain fatty acid residue in the #1 or #3 position and two long chain fatty acid residues in the remaining two positions, and "LML" represents a triglyceride with a medium chain fatty acid residue in the #2 position and two long chain fatty acid residues in the #1 and #3 positions.

By "MMM", as used herein, is meant a triglyceride containing medium chain saturated fatty acid residues at all three positions. Similarly, "LLL" represents a triglyceride containing long chain saturated fatty acid residues at all three positions.

By "stearic MCT", as used herein, is meant a mixture of reduced calorie triglycerides according to the present invention that have been prepared by combining predominantly stearic acid ($C_{18}$:0) and medium chain saturated fatty acids in some manner, for example by random rearrangement of tristearin and medium chain triglycerides. The stearic MCT will contain predominantly stearic acid as the long chain saturated fatty acid. By "behenic MCT" is meant a mixture of reduced calorie triglycerides that have been prepared by combining predominantly behenic acid (C22:0) and medium chain saturated fatty acids, for example by random rearrangement of tribehenin and medium chain triglycerides. By "stearic/behenic MCT" is meant a mixture of reduced calorie triglycerides that have been prepared by combining predominantly stearic acid, behenic acid, and medium chain saturated fatty acids.

All percentages and proportions used herein are by weight unless otherwise specified.

B. Polyol Fatty Acid Polyesters

As used herein the term "polyol fatty acid polyester" is intended to include any polyol, as defined herein, which has two or more of its hydroxyl groups esterified with fatty acid groups. Preferably, the polyol has been esterified with four or more fatty acid groups. Suitable polyol fatty acid polyesters include sucrose polyesters having on average at least four, preferably at least about five, ester linkages per molecule of sucrose; the fatty acid chains preferably have from about eight to about twenty-four carbon atoms. Other suitable polyol fatty acid polyesters are esterified linked alkoxylated glycerins, including those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544.

Additional suitable polyol fatty acid polyesters are esterified epoxide-extended polyols of the general formula P(OH) A+C (EPO)N (FE)B wherein P(OH) is a polyol, A is from 2% to about 8 primary hydroxyls, C is from about 0 to about 8 total secondary and tertiary hydroxyls, A+C is from about 3% to about 8, EPO is a $C_3$–$C_6$ epoxide, N is a minimum epoxylation index average number, FE is a fatty acid acyl moiety and b is an average number is the range of greater than 2 and no greater than A+C, as described in U.S. Pat. No. 4,861,613 and EP 0324010 A1, incorporated herein by reference. The minimum epoxylation index average number has a value generally equal to or greater than A and is a number sufficient so that greater than 95% of the primary hydroxyls of the polyol are converted to secondary or tertiary hydroxyls. Preferably the fatty acid acyl moiety has a C7–C23 alkyl chain.

Preferred esterified epoxide-extended polyols include esterified propoxylated glycerols prepared by reacting a propoxylated glycerol having from 2 to 100 oxypropylene units per glycerol with $C_{10}$–$C_{24}$ fatty acids or with $C_{10}$–$C_{24}$ fatty acid esters, as described in U.S. Pat. Nos. 4,983,329 and 5,175,323, respectively, both incorporated herein by reference. Also preferred are esterified propoxylated glycerols prepared by reacting an epoxide and a triglyceride with an aliphatic polyalcohol, as described in U.S. Pat. No. 5,304,665, incorporated herein by reference, or with an alkali metal or alkaline earth salt of an aliphatic alcohol, as described in U.S. Pat. No. 5,399,728, incorporated herein by reference. More preferred are acylated propylene oxide-extended glycerols having a propoxylation index of above about 2, preferably in the range of from about 2 to about 8, more preferably about 5 or above, wherein the acyl groups are $C_8$–$C_{24}$, preferably C14–$C_{18}$, compounds, as described in U.S. Pat. Nos. 5,603,978 and 5,641,534, both incorporated herein by reference. Particularly preferred are fatty acid-esterified propoxylated glycerols which exhibit a sharp metal before about 92 F. (33° C.) and have a dilatomeric solid fat index at 92 F. (33° C.) of less than about 30, as described in WO 97/2260, or which have a dilatomeric solid fat index of at least about 50 at 70 F. (21° C.) and at least about 10 at 98.6 F. (37° C.), as described in U.S. Pat. Nos. 5,589,217 and 5,597,605, both incorporated herein by reference.

Other suitable esterified epoxide-extended polyols include esterified alkoxylated polysaccharides. Preferred esterified alkoxylated polysaccharides are esterified alkoxylated polysaccharides containing anhydromonosaccharide units, more preferred are esterified propoxylated polysaccharides containing anhydromonosaccharide units, as described in U.S. Pat. No. 5,273,772, incorporated herein by reference.

As used herein, the term "polyol" is intended to include any aliphatic or aromatic compound containing at least two free hydroxyl groups. Suitable polyols can be selected from the following classes: saturated and unsaturated straight and branch chain linear aliphatics; saturated and unsaturated cyclic aliphatics, including heterocyclic aliphatics; or mononuclear or polynuclear aromatics, including heterocyclic aromatics. Carbohydrates and non-toxic glycols are preferred polyols.

Monosaccharides suitable for use herein include, for example, glucose, mannose, galactose, arabinose, xylose, ribose, apiose, rhamnose, psicose, fructose, sorbose, tagatose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, xylans, mannan and galactans. Although sugar alcohols are not carbohydrates in a strict sense, the naturally occurring sugar alcohols are so closely related to the carbohydrates that they are also preferred for use herein. Natural sugar alcohols which are suitable for use herein are sorbitol, mannitol, and galactitol.

Particularly preferred classes of materials suitable for use herein include the monosaccharides, the disaccharides and sugar alcohols. Preferred unesterified polyols include glucose, fructose, glycerol, polyglycerols, sucrose, xylitol, and sugar ethers. Preferred unesterified polyols also include alkoxylated polyols such as alkoxylated glycerol, alkoxylated polyglycerols, alkoxylated sorbitol, alkoxylated polysaccharides, and linked alkoxylated polyols such as linked alkoxylated glycerins. Polyols may be alkoxylated with $C_3$–$C_6$ epoxides, such as propylene oxide, butylene oxide, isobutylene oxide, and pentene oxide, to produce epoxide-extended polyols having an epoxylation index minimum of at least about 2, preferably in the range of from about 2 to about 8, as described in U.S. Pat. No. 4,816,613, incorporated herein by reference. Polyols may be also alkoxylated with an epoxide, preferably a $C_3$–$C_{10}$ 1,2-alkylene oxide, in the presence of a ring-opening polymerization catalyst, as described in U.S. Pat. Nos. 5,399,729 and 5,512,313, incorporated herein by reference.

Suitable alkoxylated polyols are described in U.S. Pat. Nos. 4,983,329; 5,175,323; 5,288,884; 5,298,637; 5,362,894; 5,387,429; 5,446,843; 5,589,217; 5,597,605; 5,603,978 and 5,641,534, all incorporated herein by reference. Suitable alkoxylated polyols include alkoxylated sugar alcohols, alkoxylated monosaccharides, alkoxylated disaccharides, alkoxylated polysaccharides, alkoxylated $C_2$–$C_{10}$ aliphatic diols, and alkoxylated $C_3$–$C_{12}$ aliphatic triols. Preferred alkoxylated $C_3$–$C_{12}$ aliphatic triols are alkoxylated glycerols, more preferred are propoxylated glycerols, and particularly preferred are propoxylated glycerols having from about 3 to about 21 moles of propylene oxide per mole glycerol. Preferred alkoxylated polysaccharides are alkoxylated polysaccharides containing anhydromonosaccharide units, more preferred are propoxylated polysaccharides containing anhydromonosaccharide units, as described in U.S. Pat. No. 5,273,772, incorporated herein by reference. Preferred linked alkoxylated glycerins include those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544. A particularly preferred polyol is propoxylated glycerin.

As used herein, the term "impurities" is intended to include a variety of constituents which are undesirable in the purified polyol fatty acid polyester product of the present invention. As will be understood, a particular component, e.g. a di- or tri-glyceride, can be an innocuous constituent of a polyol fatty acid polyester product for one application, but, on the other hand, can be undesirable, i.e. an impurity, in another application. For example, because both di- and tri-glyceride are caloric-containing fats, their presence in a polyol fatty acid polyester which is intended for use as a low calorie fat can be undesirable, whereby the glycerides would both be considered impurities. Likewise, if the polyol fatty acid polyester is intended for use as a food product, trace amounts of metals would be considered impurities if they are not appropriate for consumption by humans. Items such as breakdown products of an initial reactant which is used to form the polyol fatty acid polyester, for example the caramelized by-product of sucrose, can be both inert and suitable for consumption by an average consumer. However, by-products such as the caramelized by-product of a polyol can add undesirable color and/or adversely affect the viscosity of the polyol fatty acid polyester product. Thus, the breakdown product of the initial reactant can be considered an impurity even though it is generally inert and consumable. "Impurity", as used herein, is intended to include anything other than the desired polyol fatty acid polyester, the soap and the fatty acid lower alkyl esters as discussed in greater detail below.

The polyol fatty acid polyesters useful in the present invention comprise sugar fatty acid polyesters, sugar alcohol fatty acid polyesters, and mixtures thereof, the sugars and sugar alcohols containing from 4 to 8 hydroxy groups prior to esterification. Sugar or sugar alcohol fatty acid polyesters comprise sugars or sugar alcohols, and fatty acids. The term "sugar" is used herein in its conventional sense as generic to mono- and disaccharides. The term "sugar alcohol" is also used in its conventional sense as generic to the reduction product of sugars wherein the aldehyde or ketone group has been reduced to an alcohol. The polyol fatty acid polyesters are prepared by reacting a monosaccharide, disaccharide or sugar alcohol with fatty acids as discussed below.

Examples of suitable monosaccharides are those containing hydroxy groups such as xylose, arabinose, and ribose; the sugar alcohol derived from xylose, i.e., xylitol, is also suitable. The monosaccharide erythrose is not suitable for the practice of this invention since it only contains 3 hydroxy groups; however, the sugar alcohol derived from erythrose, i.e., erythritol, contains 4 hydroxy groups and is thus suitable. Among 5 hydroxy-containing monosaccharides that are suitable for use herein are glucose, mannose, galactose, fructose, and sorbose. A sugar alcohol derived from sucrose, glucose, or sorbose, e.g., sorbitol, contains 6 hydroxy groups and is also suitable as the alcohol moiety of the polyester compounds. Examples of suitable disaccharides are maltose, lactose, and sucrose, all of which contain 8 hydroxy groups. Preferred polyols for preparing the polyesters for use in the present invention are selected from erythritol, xylitol, sorbitol, glucose and sucrose. Sucrose is especially preferred.

The polyol starting material having at least 4 hydroxy groups must have at least 4 of these groups esterified with a fatty acid containing from 2 to 24 carbon atoms, preferably from 8 to 22 carbon atoms, and most preferably from 12 to 18 carbon atoms. Examples of such fatty acids include acetic, butyric, caproic, caprylic, capric, lauric, myristic, myristoleic, palmitic, palmitoleic, stearic, oleic, elaidic, ricinoleic, linoleic, linolenic, eleostearic, arachidonic, behenic, and erucic acid. The fatty acids can be derived from naturally occurring or synthetic fatty acids. They can be saturated or unsaturated, including positional or geometrical isomers, e.g. cis- or trans-isomers. Suitable sources of naturally occurring fatty acids include soybean oil fatty acids, cottonseed oil fatty acids, canola oil fatty acids (i.e. fatty acids derived from low euricic acid rapeseed oil), sunflower seed oil fatty acids, sesame seed oil fatty acids, safflower oil fatty acids, palm kernel oil fatty acids, and coconut oil fatty acids.

The polyol fatty acid polyesters which are especially preferred for use in the present invention must contain at least 4 fatty acid ester groups. Polyol fatty acid polyester compounds that contain 3 or less fatty acid ester groups are digested in and the products of digestion are absorbed from the intestinal tract much in the manner of ordinary triglyceride fats, whereas the polyol fatty acid polyester compounds that contain 4 or more fatty acid ester groups are substantially nondigestible and consequently nonabsorbable by the human body. It is not necessary that all of the hydroxyl groups of the polyol be esterified with fatty acids, but it is preferable that the polyol contain no more than 3 unesterified hydroxyl groups, and more preferable that it contain no more than 2 unesterified hydroxyl groups. Most preferably, substantially all of the hydroxyl groups of the polyol are esterified with fatty acids, i.e., the polyester is substantially completely esterified. The fatty acids esterified to the polyol molecule can be the same or mixed.

The present invention is particularly useful for polyol fatty acid polyesters that are liquid (i.e., minimal or no Solid Fat Content) at a temperature of 98.6° F. (37° C.), i.e., body temperature, or below. Suitable liquid polyol fatty acid polyesters typically have a viscosity of about 2 poise or less at 100° F. (37.8° C.) when measured at a shear rate of 10 sec$^{-1}$. These liquid polyesters typically contain fatty acid ester groups having a high proportion of C12 or lower fatty acid groups or else a high proportion of $C_{18}$ or higher unsaturated fatty acid groups. In the case of those liquid polyol polyesters having high proportions of unsaturated $C_{18}$ or higher fatty acid groups, at least about half of the fatty acids incorporated into the polyester molecule are typically unsaturated. Preferred unsaturated fatty acids in such liquid polyesters are oleic acid, linoleic acid, and mixtures thereof. The following are nonlimiting examples of specific liquid polyol fatty acid polyesters suitable for use in the present invention: sucrose tetraoleate, sucrose pentaoleate, sucrose hexaoleate, sucrose heptaoleate, sucrose octaoleate, sucrose octaesters of soybean oil fatty acids (unsaturated), sucrose octaesters of canola oil fatty acids, sucrose octaesters of palm kernel oil or coconut oil fatty acids, glucose tetraoleate, the glucose tetraesters of or coconut oil soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

Polyol fatty acid polyesters that are normally solid at body temperatures can also be useful in the present invention. Useful solid polyol polyesters form a mixture with the reduced calorie triglycerides (as defined hereafter) that melts at or below 98.6° F. (37.8° C.) due to eutectic or solvent effects. An example of a solid polyester capable of forming such mixtures with the reduced calorie triglycerides is a sucrose octaester having C12 to C14 fatty acid groups, and preferably predominantly myristic acid groups (i.e. at least about 90% myristic acid, and most preferably at least about 95% myristic acid).

Particularly preferred solid fatty acid polyol polyesters for use in the present invention are those materials disclosed in U.S. Pat. Nos. 5,306,514; 5,306,515; and 5,306,516, all to Letton et al., all issued Apr. 26, 1994, and all assigned to The Procter & Gamble Company. Said materials are solid polyol polyesters and referred to hereinafter as "high-$C_{20}$ and above long-chain fatty acid polyol polyesters" and comprise: (I) long chain (at least 12 carbon atoms) unsaturated fatty acid radicals, or a mixture of said radicals and saturated short chain ($C_2$–$C_{12}$) fatty acid radicals, and (ii) long chain (at least 20 carbon atoms) saturated fatty acid radicals, in a molar ratio of I:II of from about 1:15 to about 2:1, and wherein at least 4 of the hydroxyl gorups of the polyol are esterified. The polyol fatty acid polyesters suitable for use herein can be prepared by a variety of methods known to those skilled in the art. These methods include: transesterification of the polyol with methyl, ethyl or glycerol fatty acid esters using a variety of catalysts; acylation of the polyol with a fatty acid chloride; acylation of the polyol with a fatty acid anhydride; and acylation of the polyol with a fatty acid, per se. See, for example, U.S. Pat. Nos. 2,831,854, 3,600,186, 3,963,699, 4,517,360 and 4,518,772, all of which are incorporated by reference, which disclose suitable methods for preparing polyol fatty acid polyesters.

A key component of the nondigestible fat compositions herein is a liquid nondigestible oil having a complete melting point below about 37° C. Suitable liquid nondigestible edible oils for use herein include liquid polyol polyesters (see Jandacek; U.S. Pat. No. 4,005,195; Issued Jan. 25, 1977); liquid esters of tricarballylic acids (see Hamm; U.S. Pat. No. 4,508,746; Issued Apr. 2, 1985); liquid diesters of dicarboxylic acids such as derivatives of malonic and succinic acid (see Fulcher, U.S. Pat. No. 4,582,927; Issued Apr. 15, 1986); liquid triglycerides of alpha-branched chain carboxylic acids (see Whyte; U.S. Pat. No. 3,579,548; Issued May 18, 1971); liquid ethers and ether esters containing the neopentyl moiety (see Minich; U.S. Pat. No. 2,962,419; Issued Nov. 9, 1960); liquid fatty polyethers of polyglycerol (See Hunter et al; U.S. Pat. No. 3,932,532; Issued Jan. 13, 1976); liquid alkyl glycoside fatty acid polyesters (see Meyer et al; U.S. Pat. No. 4,840,815; Issued Jun. 20, 1989); liquid polyesters of two ether linked hydroxypolycarboxylic acids (e.g., citric or isocitric acid) (see Huhn et al; U.S. Pat. No. 4,888,195; Issued Dec. 19, 1988); and liquid esters of epoxide-extended polyols (see White et al; U.S. Pat. No. 4,861,613; Issued Aug. 29, 1989); as well as liquid polydimethyl siloxanes (e.g., Fluid Silicones available from Dow Corning). All of the foregoing patents relating to the liquid nondigestible oil component are incorporated herein by reference.

Preferred liquid nondigestible oils are the liquid polyol polyesters that comprise liquid sugar polyesters, liquid sugar alcohol polyesters, and mixtures thereof. The preferred sugars and sugar alcohols for preparing these liquid polyol polyesters include erythritol, xylitol, sorbitol, and glucose, with sucrose being especially preferred. The sugar or sugar alcohol starting materials for these liquid polyol polyesters are preferably esterified with fatty acids containing from 8 to 22 carbon atoms, and most preferably from 8 to 18 carbon atoms. Suitable naturally occurring sources of such fatty acids include corn oil fatty acids, cottonseed oil fatty acids, peanut oil fatty acids, soybean oil fatty acids, canola oil fatty acids (i.e. fatty acids derived from low erucic acid rapeseed oil), sunflower seed oil fatty acids, sesame seed oil fatty acids, safflower oil fatty acids, fractionated palm oil fatty acids, palm kernel oil fatty acids, coconut oil fatty acids, tallow fatty acids and lard fatty acids.

The nondigestible polyol polyesters that are liquid are those which have minimal or no solids at body temperatures (i.e., 98.6° F., 37° C.). These liquid polyol polyesters typically contain ester groups having a high proportion of C.sub.12 or lower fatty acid radicals or else a high proportion of C.sub.18 or higher unsaturated fatty acid radicals. In the case of those liquid polyol polyesters having high proportions of unsaturated C.sub.18 or higher fatty acid radicals, at least about half of the fatty acids incorporated into the polyester molecule are typically unsaturated. Preferred unsaturated fatty acids in such liquid polyol polyesters are oleic acid, linoleic acid, and mixtures thereof.

The following are nonlimiting examples of specific liquid polyol polyesters suitable for use in the present invention: sucrose tetraoleate, sucrose pentaoleate, sucrose hexaoleate, sucrose heptaoleate, sucrose octaoleate, sucrose hepta- and octaesters of unsaturated soybean oil fatty acids, canola oil fatty acids, cottonseed oil fatty acids, corn oil fatty acids, peanut oil fatty acids, palm kernel oil fatty acids, or coconut oil fatty acids, glucose tetraoleate, the glucose tetraesters of coconut oil or unsaturated soybean oil fatty acids, the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

The liquid polyol polyesters suitable for use in the compositions herein can be prepared by a variety of methods known to those skilled in the art. These methods include: transesterification of the polyol (i.e. sugar or sugar alcohol) with methyl, ethyl or glycerol esters containing the desired acid radicals using a variety of catalysts; acylation of the polyol with an acid chloride; acylation of the polyol with an acid anhydride; and acylation of the polyol with the desired acid, per se. (See, for example, U.S. Pat. Nos. 2,831,854, 3,600,186, 3,963,699, 4,517,360 and 4,518,772, all of which are incorporated by reference. These patents all disclose suitable methods for preparing polyol polyesters.)

Specific, but nonlimiting, examples of the preparation of polyol fatty acid polyesters suitable for use in the practice of the present invention are as follows.

Erythritol tetraoleate: Erythritol and a five-fold molar excess of methyl oleate are heated at 180° C. under vacuum, with agitation, in the presence of sodium methoxide catalyst over two reaction periods of several hours each. The reaction product (predominately erytiritol tetraoleate) is refined in petroleum ether and crystallized three times from several volumes of acetone at 1° C.

Xylitol pentaoleate: Xylitol and a five-fold molar excess of methyl oleate in dimethylacetamide (DMAC) solution are heated at 180° C. for five hours in the presence of sodium methoxide catalyst, under vacuum. During this time the DMAC is removed by distillation. The product (predominately xylitol pentaoleate) is refined in petroleum ether solution and, after being freed of petroleum ether, is separated as a liquid layer four times from acetone at about 1° C. and twice from alcohol at about 10° C.

Sorbitol hexaoleate is prepared by essentially the same procedure used to prepare xylitol pentaoleate except that sorbitol is substituted for xylitol.

Sucrose octaoleate is prepared by substantially the same procedure as that used to prepare erythritol tetraoleate except that sucrose is substituted for erythritol. Sucrose octaesters of soybean oil fatty acids: Soybean oil is partially hydrogenated to an iodine value of 107 and then converted to the respective methyl esters. These methyl esters are then reacted with sucrose in the presence of a potassium carbonate catalyst and the potassium soap of the soybean oil fatty acids.

Sucrose octaesters of canola oil fatty acids: Canola oil is partially hydrogenated to an iodine value of 90 and then converted to the respective methyl esters. These methyl esters are then reacted with sucrose at about 135° C. in the presence of a-potassium carbonate catalyst and the potassium soap of the canola oil fatty acids. See Example 1 of U.S. Pat. No. 4,517,360 to Volpenhein, issued May 14, 1985. Sucrose octaesters of soybean hardstock/soybean oil fatty acids: See Examples 1 and 2 of European patent application 236,288 to Bernhardt, published Sep. 9, 1987.

Sucrose octaesters of predominantly myristic acid: Myristic acid (at least 99% pure) is converted to the respective methyl esters. These methyl esters are then reacted with sucrose at about 135° C. in the presence of a potassium carbonate catalyst and the potassium soap of myristic acid. See Example 2 (reaction conditions) and 1 (wash conditions) of U.S. Pat. No. 4,517,360 to Volpenhein, issued May 14, 1985.

Sucrose octaesters of palm kernel oil fatty acids: Palm kernel oil(hydrogenated to an iodine value of about 4) is converted to the respective methyl esters. These methyl esters are the respective methyl esters. These methyl esters are then reacted with sucrose at about 135° C. in the presence of a potassium carbonate catalyst and the potassium soap of the palm kernel oil fatty acids. See Example 1 of U.S. Pat. No. 4,517,360 to Volpenhein, issued May 14, 1985.

C. Reduced Calorie Triglycerides

The reduced calorie triglycerides useful in the present invention are selected from MMM, MLM, MML, LLM, LML, and LLL triglycerides and particularly mixtures thereof, wherein M is a saturated fatty acid residue selected from $C_6$ to $C_{10}$ saturated fatty acids, and mixtures thereof, and L is a saturated fatty acid residue selected from $C_{18}$ to $C_{24}$ saturated fatty acids, and mixtures thereof. See U.S. application entitled "Reduced Calorie Fats Made from Triglycerides Containing Medium and Long Chain Fatty Acids" to Paul Seiden, Ser. No. 329,620, filed Dec. 4, 1992, now U.S. Pat. No. 5,288,512 (herein incorporated by reference), which discloses reduced calorie fats comprising reduced calorie triglycerides useful in the present invention, and especially Examples 1 and 2 for methods for making same. The reduced calorie triglycerides comprise: (1) at least about 85%, preferably at least about 90%, and most preferably at least about 95% combined MLM, MML, LLM and LML triglycerides.

For some of the fat compositions of the present invention, for example fat compositions to be incorporated into chocolate products, mono-long chain triglycerides (MLM and MML) are preferred over di-long chain triglycerides (LLM and LML), as well as the tri-long chain (LLL) and tri-medium chain (MMM) triglycerides. For these applications, the reduced calorie triglycerides comprise: (1) at least about 80%, preferably at least about 90% and most preferably at least about 95% combined MLM and MML triglycerides; (2) no more than about 10%, preferably no more than about 5%, and most preferably no more than about 2% combined LLM and LML triglycerides; (3) no more than about 8%, preferably no more than about 4%, and most preferably no more than about 3% MMM triglycerides; and (4) no more than about 2%, preferably no more than about 1%, and most preferably no more than about 0.5% LLL triglycerides. For other applications, such as where the reduced calorie fat composition is to be used as a frying oil, di-long chain triglycerides may be preferred.

In the reduced calorie triglycerides of the present invention, the medium chain fatty acids generally control the melting point of the respective triglyceride mixture. In particular, it has been found that these medium chain saturated fatty acids, when esterified onto the glycerol molecule, lower the melting point of the resulting triglyceride. In addition, these medium chain fatty acids are readily hydrolyzed (especially if attached at the #1 or #3 positions) by pancreatic lipase and then absorbed to provide a rapid energy source. However, these medium chain fatty acids, when metabolized, provide less total calories (per gram) than the longer chain fatty acids.

The fatty acid composition of reduced calorie triglycerides useful in the present invention comprise from about 10% to about 70%, preferably from about 20% to about 65%, more preferably from about 30 to 60%, and most preferably from about 40% to about 50% $C_6$ to $C_{10}$ saturated fatty acids. The C 8 and C 10 saturated fatty acids are most preferred for use in the reduced calorie triglycerides of the present invention in combination with the $C_{18}$ to $C_{24}$ long chain saturated fatty acids. These long chain saturated fatty acids, when hydrolyzed from the respective triglyceride, are generally much more poorly absorbed compared to the medium chain saturated fatty acids and long chain unsaturated fatty acids, e.g. linoleic acid. This is especially true as the fatty acid increases in chain length from C 18 (stearic) to C 22 (behenic) or higher. These poorly absorbed long chain fatty acids are generally solid at a temperature of 98.6° F. (37° C.).

The reduced calorie triglycerides of the present invention comprise from about 30% to about 90%, preferably from about 40% to about 80%, more preferably from about 40% to about 70%, and most preferably from about 45% to about 60% $C_{18}$ to $C_{24}$ saturated fatty acids. For behenic MCT's, the reduced calorie triglycerides comprise from about 20% to about 80%, preferably from about 30% to about 70%, and most preferably from about 40% to about 60% C20 to $C_{24}$ long chain saturated fatty acids. Preferred behenic MCT's have fatty acid compositions which comprise no more than about 12%, and most preferably no more than about 9% C20 to $C_{24}$ saturated fatty acids other than C22 (behenic) saturated fatty acid. For stearic/behenic MCT's, the reduced calorie triglycerides preferably comprise from about 10% to about 30% $C_{18}$ (stearic) saturated fatty acid.

The reduced calorie triglycerides of the present invention can contain minor amounts of other fatty acids besides medium and long chain saturated fatty acids, without losing the benefits of the present invention. For example, small amounts of C12:0, C14:0, C16:0, $C_{18:1}$, $C_{18:2}$ and $C_{18:3}$ fatty acids can be present. Palnitic acid (C16:0) is about 95% absorbed by the body, while the longer chain saturated fatty acids are less absorbed. Therefore, it is preferred that the reduced calorie triglycerides comprise no more than about 30% C16:0 fatty acid, preferably no more than about 10% C16:0 fatty acid and most preferably no more than about 20% C16:0 fatty acid.

The reduced calorie triglycerides also typically comprise no more than about 25%, preferably no more than about 15% and more preferably no more than about 6% fatty acids selected from $C_{18:1}$, $C_{18:2}$ and $C_{18:3}$ unsaturated fatty acids, and mixtures thereof, and most preferably no more than about 0.5%. Preferred reduced calorie triglycerides also comprise no more than about 25%, preferably no more than about 15%, and most preferably no more than about 3% fatty acids selected from C12:0 (lauric) and C14:0 (myristic) fatty acids, and mixtures thereof. Lauric and myristic acids result in more fat deposition than medium chain saturated fatty acids.

Preferred stearic MCTs useful in the present invention comprise at least about 80% triglycerides having carbon number of from $C_{34}$ to $C_{38}$, from about 30% to about 50%, preferably from about 40% to about 50% $C_8$ to $C_{10}$ saturated fatty acids and from about 30% to about 70%, most preferably from about 40% to about 60% stearic acid. Preferred behenic MCT's comprise at least about 80% triglycerides having carbon numbers of from $C_{34}$ to $C_{42}$, from about 30% to about 50%, preferably from about 40% to about 50% $C_8$ to $C_{10}$ saturated fatty acids and from about 30% to about 70%, preferably from about 40% to about 60% behenic acid. Preferred stearic/behenic MCT's preferably comprise at least about 80% triglycerides having carbon numbers of from $C_{34}$ to $C_{42}$, from about 30% to about 50%, preferably from about 40% to about 50% $C_8$ to $C_{10}$ saturated fatty acids and from about 30% to about 70%, preferably from about 40% to about 60% combined stearic and behenic acid.

The reduced calorie triglycerides of the present invention can be prepared by a wide variety of techniques such as:

(a) random rearrangement of long chain triglycerides (e.g. tristearin or tribehenin) and medium chain triglycerides;

(b) esterification of glycerol with a blend of the corresponding fatty acids;

(c) transesterification of a blend of medium and long chain fatty acid methyl esters with glycerol; and (d) transesterification of long chain fatty acid glycerol esters (e.g., glyceryl behenate) with medium chain triglycerides.

Random rearrangement of triglycerides is well-known in the art, as is the esterification of glycerol with fatty acids. For discussions on these subjects, see Hamilton et al., Fats and Oils: Chemistry and Technology, pp. 93–96, Applied Science Publishers Ltd., London (1980), and Swern, Bailey's Industrial Oil and Fat Products, 3d ed., pp. 941–943 and 958–965 (1964), both disclosures incorporated by reference herein. Transesterification is also discussed generally in Bailey's at pp. 958–963.

Fatty acids per se or naturally occurring fats and oils can serve as sources of fatty acids for preparing the reduced calorie triglycerides. For example, hydrogenated soybean oil and hydrogenated high erucic acid rapeseed oil are good sources of stearic and behenic acid, respectively. Odd chain length long chain saturated fatty acids can be found in certain marine oils. Medium chain saturated fatty acids can be obtained from coconut, palm kernel, or babassu oils. They can also be obtained from commercial medium chain triglycerides, such as the Captex 300 brand sold by Capital City Products, of Columbus, Ohio.

Tribehenin, useful for making the present reduced calorie triglycerides, can be prepared from behenic acid or from fractionated methyl behenate by esterification of the acid, or by transesterification of methyl behenate with glycerol. More importantly, blends of behenic acid and medium chain saturated fatty acids can be esterified with glycerol. Other long chain saturated fatty acids ($C_{18}$, C20, etc.) can be included as well. Similarly, methyl ester blends can also be interesterified with glycerol. The reduced calorie triglycerides can be modified to satisfy specific product performance requirements by additional fractionation. Solvent and non-solvent crystal fractionation or fractional distillation methods (e.g. molecular distillation as described below) can be applied to optimize performance. Standard fractionetlon methods are discussed in Applewhite, Bailey's Industrial Oil and Fat Products, Vol. 3, 4th ed. (1985), pp. 1–39, John Wiley & Sons, New York, incorporated by reference herein. Molecular distillation can separate MML/MLM from LLM/LML-type triglycerides, and can shift the carbon number concentration, but it cannot fractionate triglycerides having the same carbon number. Non-solvent or solvent crystal fractionation can also fractionate MLM/MML-type triglycerides from the higher melting LLM/LML triglycerides. The behenic MCT's fractionate without a solvent at about 70° F. (21° C.), while the stearic/behenic MCT's fractionate at about 60° F. (16° C.). Crystallization and filtration are usually repeated two or three times.

Fractional distillation of the present reduced calorie triglycerides is not limited to molecular distillation, but can also include conventional distillation (continuous or batch). After synthesis of the crude triglyceride mixture, it is common to use a conventional batch distillation technique to remove most of the excess medium chain triglycerides, and then continue with molecular distillation. The vacuum requirements are not as strict, and the temperature used can be higher in conventional distillation versus molecular distillation. The conventional distillation temperature is generally between 405° F. (207° C.) and 515° F. (268.3° C.). The absolute pressure is less than 8 mm Hg, more preferably less than 2 mm Hg. The distillation is aided by sparging with steam, nitrogen or other inert gas (e.g., C2). The distillation is carried out to remove part of the excess MCT, most of the excess MCT, or to distill also the mono-long chain (MLM and MML) components.

Crystal fractionation of the fats can be carried out with and without solvents, with and without agitation. The crystal fractionation can be repeated several times. Crystal fractionation is particularly effective to remove high melters. Fractionation of behenic MCT without solvents can be used to remove carbon number 50 and 52 LLM and LML components, which in turn alters the melting profile.

D. Reduced Calorie Fat Compositions

The present invention particularly relates to reduced calorie fat compositions which are based on combinations of the polyol polyesters defined in Section B with the reduced calorie triglycerides defined in Section C.

In the reduced calorie fat compositions of the present invention, the particular level of polyol polyester that is included will depend on a number of factors, including the application for which the composition is used, the particular properties that are desired, as well as the physical properties of the polyol polyester. Suitable reduced calorie fat compositions of the present invention can comprise from about 10% to about 95% of such polyol polyesters; the specific amounts being largely determined by the solids level at body temperature (98.6° F., 37° C.). When the polyol polyesters are entirely liquid (i.e., have a melting point less than or equal to 37° C.), or comprise <3% solids at body temperature (98.6° F., 37° C.), or comprise preferred compositions comprised from about 65% to about 85%, more preferably from about 65% to about 80%, and most preferably from about 65% to about 75% polyol polyesters. When the polyol polyesters incorporate at least about 3% solid polyol polyesters (i.e., having a melting point of about 37° C. or greater) ≧3% solids at body temperature (98.6° F., 37° C.), then the reduced calorie fat compositions of the present invention preferably comprise from about 10% to about 95% of such polyol polyesters, and most preferably from about 65% to about 95% of such polyesters.

The particular polyol polyester used in the reduced calorie fat compositions of the present invention will frequently depend on the particular application in which it is used. For example, for cooking and salad oils, liquid polyol polyesters are typically used such as sucrose octaesters of soybean oil or canola oil fatty acids. Frying oils for salted snacks and other fried foods also typically comprise liquid polyol polyesters, alone or in combination with more viscous polyol polyesters such as sucrose octaesters of soybean hardstock/soybean oil fatty acids. In the case of ice creams and ice cream coatings, sucrose octaesters of palm kernel oil or coconut oil fatty acids are preferred due to the sharper melting profile of the polyol polyester. For firm chocolate applications such as chocolate candy bars and chocolate chips, sucrose octaesters having predominately myristic acid groups are preferred.

In terms of caloric reduction, the polyol polyesters used in the fat compositions of the present invention essentially provide minimal or fewer calories since they are largely nondigestible, and therefore largely nonabsorbable- Unfortunately, regular ingestion of moderate to high levels of liquid versions of these polyesters can produce undesirable "laxative" side effects, namely, leakage of these polyesters through the anal sphincter. As disclosed in U.S. Pat. No. 4,005,195 to Jandacek, one way to prevent this undesirable laxative side effect is to include in the liquid polyol polyesters anti-anal leakage (AAL) agents which are completely solid at body temperature, including solid versions of these polyesters. However, inclusion of these solid AAL agents in the liquid polyesters at sufficiently high levels can impart a less than desirable textural feel in the mouth typically referred to as "waxiness". These solid AAL agents can also cause the resulting fat product, such as a cooking and salad oil, to be opaque, rather than clear at room temperature or below.

It has been surprisingly found that the reduced calorie triglycerides defined in Section C, when used in an effective amount, can provide AAL benefits for the liquid polyol polyesters, without at the same time imparting an undesirable waxy mouthfeel. While not wishing to be bound by theory, it is believed that the saturated long chain fatty acids present in these reduced calorie triglycerides, when hydrolyzed by pancreatic lipase, form solid AAL materials in situ in the gut. These solid long chain saturated fatty acids (or their soaps) act to bind the liquid polyol polyesters so as to avoid liquid oil separation from the fecal matrix and associated oil leakage through the anal sphincter. The AAL benefit of these reduced calorie triglycerides is particularly enhanced by the inclusion of small amounts (e.g., from about 0.05% to about 0.2% of the composition) of certain soaps of saturated C12 and higher fatty acids, in particular soaps of stearic and behenic fatty acids. These soaps include sodium and potassium water-soluble soaps, as well as calcium and magnesium water-insoluble soaps. Preferred soaps for inclusion in the reduced calorie fat compositions of the present invention are calcium behenate and magnesium stearate.

It is also believed that these reduced calorie triglycerides provide AAL benefits for fat compositions containing polyol polyesters that are more viscous or solid at body temperatures. For example, sucrose octaesters of soybean hardstock/soybean oil fatty acids are still somewhat viscous at 98.6° F. (37° C.) due to an appreciable level of solids that bind the liquid portion of the polyesters. This viscous system is usually sufficient to provide anal leakage control for non-heated applications such as margarines, frozen desserts and the like. However, in heated applications, such as cooking or particularly frying, these sucrose octaesters of soybean hardstock/soybean oil fatty acids can remain liquid for a sufficient period of time to cause a potential anal leakage problem. Similarly, solid polyol polyesters that melt at or below 98.6° F. (37° C.) due to solvent/eutectic effects of the reduced calorie triglycerides may also be subject to potential leakage problems. It is believed the saturated long chain fatty acids present in the reduced calorie triglycerides would prevent potential anal leakage of these more viscous or solid polyol polyesters by a mechanism similar to that for the liquid polyol polyesters.

The particular level of reduced calorie triglycerides required for AAL benefits will depend on the composition of the reduced calorie triglycerides, in particular the level of long chain saturated fatty acids present in the triglycerides, as well as the physical properties of the polyol-polyester. To provide anti-anal leakage benefits, the reduced calorie triglycerides are included in the fat composition in an amount of from about 5% to about 90%. Preferably, these reduced calorie triglycerides are included in the fat composition in an amount of from about 15% to about 35%, more preferably in an amount of from about 20% to about 35%, and most preferably from about 25% to about 35% when they are combined with polyol polyesters that are entirely liquid, or comprise >3% solids at body temperature (98.6° F., 37° C.). If at least 3% solid polyol polyester is included in the polyol polyester or the polyol polyester comrpises ≧3% solids at body temperature (98.6° F., 37° C.), then from about 5% to about 90%, preferably about 15% to about 35% reduced calorie triglycerides are used in the reduced calorie fat compositions of the present invention. Although not required for AAL benefits, higher levels of these reduced calorie triglycerides, i.e. from about 60% to about 90%, may be desired when the polyol polyester is a liquid.

In vivo testing is preferably used to determine the ability of the reduced calorie triglycerides to provide the desired AAL benefits. In such testing, animals are given a diet containing a reduced calorie fat composition comprising a polyol polyester and a reduced calorie triglyceride. The fecal output of the animals is then monitored for consistency (i.e. loose stools) and for liquid oil separation for the fecal matrix, which are generally predictive of the risk of oil leakage through the anal sphincter.

The combination of the reduced calorie triglycerides with the polyol polyesters can also provide additional benefits. With regard to more viscous or solid polyol polyesters, these reduced calorie triglycerides can provide significant textural/taste benefits. For example, the more viscous polyol polyesters such as the sucrose octaesters of soybean hardstock/soybean oil fatty acids, have an appreciable level of solids, even at body temperatures. The reduced calorie triglycerides act as a solvent to reduce the level of solids in these more viscous polyol polyesters at body temperatures. This imparts a less waxy/greasy taste when the reduced calorie fat composition is consumed. Even more surprising are the benefits obtained with solid polyol polyesters, such as sucrose octaesters containing predominantly myristic acid groups. Due to solvent/eutectic effects, the reduced calorie triglycerides can effectively lower the melting point of these solid sucrose octaesters to 98.6° F. (37° C.) or below. This provides improved mouthmelt properties that are particularly desirable for firm chocolate-flavored products.

With regard to liquid polyol polyesters, these reduced calorie triglycerides may provide benefits in terms of less oxidation during cooking and especially flying. Because liquid polyol polyesters used in these compositions can include fairly high levels of unsaturated fatty acid residues, there is the possibility of oxidation and polymerization of these unsaturated residues during cooking or frying. Because the reduced calorie triglycerides contain typically minimal levels of unsaturated fatty acids, this oxidation and polymerization problem is minimized by their inclusion in place of the liquid polyol polyesters. On the other hand, due to the high level of medium chain saturated fatty acids present, these reduced calorie triglycerides tend to have lower smoke, flash and firepoint temperatures compared to standard digestible triglycerides (e.g., soybean oil), as well as potential foaming and autoignition problems, when used in cooking or frying applications. The liquid polyol polyesters have much higher smoke, flash and firepoint temperatures. Therefore, combinations of these liquid polyol polyesters with the reduced calorie triglycerides provide reduced calorie fat compositions which have anti-anal leakage characteristics, improved oxidative characteristics during cooking or flying, while at the same time avoiding potential foaming and autoignition problems.

E. Uses of Reduced Calorie Fat Compositions

The reduced calorie fat compositions of the present invention can be used as a partial or total replacement for normal triglyceride fat in any fat-containing food product comprising fat and nonfat ingredients to provide reduced calorie benefits. In order to obtain a significant reduction in calories, at least about 10%, and preferably at least about 50%, of the total fat in the food product comprises the reduced calorie fat composition. On the other hand, very low calorie and thus highly desirable food products of the present invention are obtained when the total fat comprises up to 100% of the reduced calorie fat composition. The present reduced calorie fat compositions are useful in a wide variety of food and beverage products. For example, the fat compositions can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods, and other baked salted snacks.

In addition to their uses in baked goods, the reduced calorie fat compositions can be used alone or in combination with other regular, reduced calorie or zero calorie fats to make shortening and oil products. The other-fats can be synthetic or derived from animal or vegetable sources, or combinations of these. Shortening and oil products include, but are not limited to, shortenings, margarines, spreads, butter blends, lards, cooking and frying oils, salad oils, popcorn oils, salad dressings, mayonnaise, and other edible oil products. When the reduced calorie fat compositions of the present invention are blended with digestible triglyceride vegetable oils (such as soybean oil), to make shortening and oil products, the final blend typically comprises from about 25% to about 100%, preferably from about 50% to about 100%, and most preferably from about 75% to about 100% of the reduced calorie fat composition.

The present reduced calorie fat compositions have been found to be especially useful as partial or complete replacements for digestible triglyceride oils in frying oils used in preparing salted snack products, such as potato chips. Frying oils substituted with up to about 60% of a more viscous polyol polyester (e.g., sucrose octaesters of soybean hardstock/soybean oil fatty acids) that inherently has sufficient solids at body temperatures to provide anal leakage control have been found to impart a more waxy mouthfeel to fried potato chips. Frying oils substituted with up to about 50% of a liquid polyol polyester (e.g., sucrose octaesters of soybean oil fatty acids) have been found to be equivalent in waxiness impression to 100% triglyceride frying oils, but with the potential risk of causing anal leakage. Frying oils based on the present reduced calorie fat compositions permit the inclusion (in whole or in part) of liquid polyol polyesters to minimize the waxy mouthfeel impression imparted to fried snack products, while at the same time preventing anal leakage.

These frying oils, for use in preparing salted snacks, can comprise from about 50 to 100% reduced calorie fat composition and from 0 to about 50% digestible triglyceride oil.

Preferably, these frying oils comprise from about 75 to 100% reduced calorie fat composition, and from 0 to about 25% digestible triglyceride oil. In addition to potato chips, these frying oils can be used in the preparation of other salted snacks such as corn chips, tortilla chips, curls, puffs, potato sticks, French fries, and shoestring potatoes, as well as other fried foods such as doughnuts, fried pies (e.g., turnovers), crullers, fried meats (e.g., pork rinds and beef Jerky), fried poultry (e.g., turkey and chicken) and fried seafood (e.g., shrimp and fish).

By "digestible triglyceride oil" as used herein is meant a triglyceride oil which is typically at least about 90% digestible and which has Solid Fat Content (SFC) values of:
 (a) about 10% or less at 50° F. (10° C.); and
 (b) 0% at 70° F. (21.1° C.).

The SFC values can be determined by heating the triglyceride oil to 140° F. (60° C.) for at least 20 minutes, tempering the heated oil at 32° F. (0° C.) for at least 5 minutes, further tempering the triglyceride oil at 80° F. (26.7° C.) for at least 30 minutes and then measuring the solids content of the tempered oil by pulsed nuclear magnetic resonance (PNMR). See Madison et al., J. Amer. Oil Chem. Soc., Vol. 55 (1978), pp. 328–31, which describes the method for measuring SFC values of a fat by PNMR.

Suitable digestible triglyceride oils can be derived from animal, vegetable or marine sources, including naturally occurring oils such as cottonseed oil, soybean oil, sunflower oil, corn oil, peanut oil, safflower oil, rapeseed oil, canola oil and the like. Triglyceride oils most preferably used are soybean oil, safflower oil, sunflower oil, canola oil, and blends thereof. Triglyceride oils high in solids content such as cottonseed oil, palm oil or hydrogenated vegetable oils usually need to be winterized to provide suitable triglyceride oils having the above-defined SFC values.

Certain of the present reduced calorie fat compositions are particularly useful in the formulation of firm chocolate-flavored products such as chocolate-flavored candy bars and chocolate-flavored chips. Reduced calorie fat compositions useful in such products comprise from about 40% to about 60% of a sucrose octaester having C12 to C14 fatty acid groups (preferably predominantly myristic acid groups) and from about 40% to about 60% reduced calorie triglycerides (preferably behenic MCT's). Preferably, such reduced calorie fat compositions comprise from about 45% to about 55% of such sucrose octaesters and from about 45% to about 55% of the reduced calorie triglycerides. Sucrose octaesters having C12 to C14 fatty acid groups, especially those having predominantly myristic acid groups, melt at a temperature above 98.6° F. (37° C.). Surprisingly, it has been found that the formulation of these sucrose octaesters with reduced calorie triglycerides causes the resulting reduced calorie fat composition to melt at a temperature of about 98.6° F. (37° C.) or below. This lowering of melting point is believed to be due to either eutectic or solvent effects.

Certain of these reduced calorie fat compositions are useful in providing a portion or all of the total fat in cooking and salad oils which are clear at room temperature, i.e., at about 70° F. (21.1° C.), or below, e.g. at about 50° F. (10° C.). These cooking and salad oils comprise 25%–100% of a reduced calorie fat composition comprising:
 a. from about 65% to about 85% of a liquid polyol fatty acid polyester as defined in Section B;
 b. from about 15% to about 35% reduced calorie triglycerides as defined in Section C wherein the reduced calorie triglycerides comprise: (1) at least about 80% combined MLM and MML triglycerides; (2) no more than about 10% combined LLM and LML triglycerides; (3) no more than about 8% MMM triglycerides; and (4) no more than about 2% LLL triglycerides; and wherein the fatty composition of the reduced calorie triglycerides comprises: (1) from about 30% to about 60% $C_6$ to $C_{10}$ saturated fatty acids; (2) from about 10% to about 50% C20 to $C_{24}$ saturated fatty acids; and (3) up to about 40% $C_{18}$ saturated fatty acid; and from about 0% to about 75% of a digestible triglyceride oil as previously defined in this Section with regard to frying oils.

Preferred cooking and salad oils comprise from about 50% to about 75% of the above reduced calorie fat composition and from about 25% to about 50% digestible triglyceride oil. Reduced calorie triglycerides for use in these preferred cooking and salad oils comprise at least about 90% (most preferably at least about 95%) combined MLM and MML triglycerides, no more than about 6% (most preferably no more than about 2%) combined LLM and LML triglycerides, no more than about 3% (most preferably no more than about 2%) MMM triglycerides, no more than about 1% (preferably no more than about 0.5%) LLL triglycerides, from about 40% to about 50% $C_8$ to $C_{10}$ saturated fatty acids, from about 20% to about 50% behenic acid, and up to 30% stearic acid.

Other uses for the reduced calorie fat compositions of the present invention include partial or complete replacement for triglyceride fat and/or oils present in peanut butter, frozen desserts such as ice cream and ice cream coatings, whipped toppings, frosting products, processed meat products, including vegetable protein-based meat analog products, sauces, gravies, and dairy products such as milkshakes, milk products, coffee whiteners, and cheese products.

The present reduced calorie fat compositions can also be fortified with vitamins and minerals, particularly the fat-soluble vitamins. U.S. Pat. No. 4,034,083 of Mattson (incorporated by reference herein) discloses polyol fatty acid polyesters fortified with fat-soluble vitamins. The fat-soluble vitamins include vitamin A, vitamin D, vitamin E, and vitaminK. Vitamin A is a fat-soluble alcohol of the formula C20 C29 OH. Natural vitamin A is usually found esterified with a fatty acid; metabolically active forms of vitamin A also include the corresponding aldehyde and acid. Vitamin D is a fat-soluble vitamin well known for use in the treatment and prevention of rickets and other skeletal disorders. Vitamin D comprises sterols, and there are at least 11 sterols with vitamin D-type activity. Vitamin E (tocopherol) is a third fat-soluble vitamin, which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are C1 (phylloquinone), C2 (menaquinone), and C3 (menadione). The amount of the fat-soluble vitamins employed herein to fortify the present fat compositions can vary. If desired, the fat compositions can be fortified with a recommended daily allowance (RDA), or increment or multiple of an RDA, of any of the fat-soluble vitamins or combinations thereof. It is preferred that shortenings and oils containing up to 35% by weight of sucrose fatty acid polyesters be supplemented with 1.1 mg. vitamin E in the form of d-alpha-tocopherol acetate per gram of sucrose polyester. If used for deep frying, the shortenings and oils preferably contain 0.88 mg. vitamin E per gram of sucrose polyester.

Vitamins that are insoluble in fat can similarly be included in the present reduced calorie fat compositions. Among these vitamins are the vitamin B complex vitamins, and vitamin C. The minerals include the wide variety of minerals known to be useful in the diet, such as calcium, magnesium, and zinc. Any combination of vitamins and minerals can be used in the present reduced calorie fat compositions.

The present reduced calorie fat compositions are particularly useful in combination with particular classes of food and beverage ingredients. For example, an extra calorie reduction benefit is achieved when the fat compositions are used with noncaloric or reduced calorie sweeteners alone or in combination with bulking agents. Noncaloric or reduced calorie sweeteners include, but are not limited to, aspartame; saccharin; alltame, thaumatin; dihydrochalcones; cyclamates; steviosides; glycyrrhizins, synthetic alkoxy aromatics, such as Dulcin and P4000; sucralose; suosan; miraculin; monellin; sorbitol, xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem aminoallces, meta-aminobenzoic acid, L-aminodicarboxylic acid alkaes, and amides of certain alpha-aminodicarboxylic acids and gem-diamines; and 3-hydroxy4-alkyloxyphenyl aliphatic carboxylates or heterocyclic aromatic carboxylates.

The reduced calorie fat compositions can be used in combination with other noncaloric or reduced calorie fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the fat materials are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Bulking or bodying agents are useful in combination with the reduced calorie fat compositions in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g. lactose.

Similarly, food and beverage compositions can be made that combine the present reduced calorie fat compositions with dietary fibers to achieve the combined benefits of each. By "dietary fiber" is meant complex carbohydrates resistant to digestion by manunalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g. cellulose), a composite dietary fiber (e.g. citrus albedo fiber containing cellulose and pectin), or some combination of fibers (e.g. cellulose and a gum). The fibers can be processed by methods known to the art.

Of course, judgment should be exercised to make use of appropriate reduced calorie fat compositions and combinations of the fat compositions with other food ingredients. For example, a combination of sweetener and fat composition would not be used where the specific benefits of the two are not desired. The fat compositions and fat composition/ingredient combinations are used where appropriate, and in the proper amounts.

Many benefits are obtained from the use of the present reduced calorie fat compositions in food and beverage compositions, either when used alone or in combination with the ingredients discussed above. A primary benefit is the calorie reduction achieved when the fat compositions are used as a total or partial fat replacement. This calorie reduction can be increased by using combinations of the present fat compositions with reduced calorie sweeteners, bulking agents, or other reduced calorie or noncaloric fats. Another benefit which follows from this use is a decrease in the total amount of fats in the diet. Foods or beverages made with the reduced calorie fat compositions instead of triglyceride fats will also contain less cholesterol, and the ingestion of these foods can lead to reduced serum cholesterol and thus reduced risk of heart disease. A related benefit is that the use of the reduced calorie fat compositions allows the production of foods and beverages that are stable in terms of shelf stability and penetration stability. Compositions made with the reduced calorie fats have acceptable organoleptic properties, particularly taste and texture.

Dietary foods can be made with the reduced calorie fat compositions to meet special dietary needs, for example, of persons who are obese, diabetic, or hypercholesterolemic. The fat compositions can be a major part of a low-fat, low-calorie, low-cholesterol diet, and they can be used alone or in combination with drug therapy or other therapy. Combinations of food or beverage products made with the reduced calorie fat compositions can be used as part of a total dietary management regimen, based on one or more of these products, containing the fat compositions alone or in combination with one or more of the above-mentioned ingredients, to provide one or more of the above-mentioned benefits.

This discussion of the reduced calorie fat composition uses, combinations, and benefits, is not intended to be limiting or all-inclusive. It is contemplated that other similar uses and benefits can be found that will fall within the spirit and scope of this invention.

It is known that certain fatty esters will inhibit the absorption of cholesterol. The present invention also encompasses methods for lowering serum cholesterol by inhibiting the absorption of cholesterol without causing an anal leakage effect, comprising systemically (generally, orally) administering to animals susceptible to or afflicted with hypercholesterolemia successive therapeutically effective doses of the reduced calorie fat compositions of the foregoing type. Generally the dosage is about 0.1 gram to about 20 grams of the present fat compositions.

F. Analytical Methods

1. Solid Fat Content Measurement of Polyol Polyesters

Before determining SFC values, the sample of the polyol polyester is heated to a temperature of 158° C. (70° F.) or higher for at least 0.5 hours or until the sample is completely melted. The melted sample is then tempered at a temperature of 40° F. (4.4° C.) for at least 72 hours. After tempering, the SFC value of the sample at a temperature of 98.6° F. (37° C.) is determined by pulsed nuclear magnetic resonance (PNMR). The method for determining SFC values by PNMR is described in Madison and Hill, J. Amer. Oil Chem. Soc., Vol. 55 (1978), pp. 328–31 (herein incorporated by reference). Measurement of SFC by PNMR is also described in A.O.C.S. Official Method Cd. 16–81, Official Methods and Recommended Practices of The American Oil Chemists Society, 3rd. Ed., 1987 herein incorporated by reference).

2. Fatty Acid Composition
   a. Polyol Polyesters

The fatty acid composition (FAC) of the polyol polyesters is determined by gas chromatography, using a Hewlett-Packard Model S712A gas chromatograph equipped with a thermal conductivity detector and a Hewlett-Packard Model 7671A automatic sampler. The chromatographic method used is described in Official Methods and Recommended Practices of the American Oil Chemists Society, 3rd Ed., 1984, Procedure Ce 1–62.

b. Reduced Calorie Triglycerides

The fatty acid composition (FAC) of the reduced calorie triglycerides is measured by gas chromatography. First, fatty acid ethyl esters of the triglycerides are prepared by any standard method (e.g., by transesterification using sodium ethoxide), and then separated on a capillary column which is coated with DB-WAX stationary phase. The fatty acid ethyl esters are separated by chain length and degree of unsaturation. A split injection is made with flame ionization detection. Quantitation is performed by use of a double internal standard method (i.e., C9 and C21 triglycerides). This method can separate fatty acid ethyl esters from $C_6$ to $C_{24}$.

| Equipment | |
|---|---|
| Gas Chromatograph | Hewlett-Packard 5890, or equivalent, equipped with a split injector and flame ionization detector, Hewlett-Packard Co., Scientific Instruments Div., 1601-T California Ave., Palo Alto, CA 94304 |
| Autosampler | Hewlett-Packard 7673A, or Injector equivalent |
| Column | 15 m .times. 0.25 mm I.D., fused silica capillary column coated with DB-WAX (0.25 micron film thickness), Hewlett-Packard Co., Scientific Instruments Div. |
| Data System | Hewlett-Packard 3350, 3000-T Hanover St., Palo Alto, CA 94304 Kipp & Zonen, BD40, Kipp & Zonen |
| Reagent | |
| Hexane | Burdick & Jackson, or equivalent, American Scientific Products |

Reference Standards

Two reference standards are used each day of operation to verify proper operation of this method. 1) A reference mixture of fatty acid methyl esters (FAME) is used to check the operation of the instrument. This reference mixture has the following fatty acid composition: 1% $C_{14:0}$, 4% $C_{16:0}$, 3% $C_{18:0}$, 45% $C_{18:1}$, 15% $C_{18:2}$, 3% $C_{18:3}$, 3% $C_{20:0}$, 3% $C_{22:0}$, 20% $C_{22:1}$, and 3% $C_{24:0}$, 2) A reference standard of a commercial shortening is used to check the operation of the total system-ethylation and gas chromatographic analysis. The shortening reference standard has the following fatty acid composition: 0.5% $C_{14:0}$, 21.4% $C_{16:0}$, 9.2% $C_{18:0}$, 40.3% $C_{18:1}$, 23.0% $C_{18:2}$, 2.2% $C_{18:3}$, 0.4% $C_{10:0}$, 1.3% $C_{20:1}$, and 0.3% $C_{22:0}$.

The reference mixture of FAME should be diluted with hexane and then injected into the instrument. A new vial of FAME reference mixture should be opened every day since the highly unsaturated components, $C_{18}$:2 and $C_{18}$:3, oxidize easily. The shortening reference standard should be ethylated with the samples prior to their analysis by capillary gas chromatography. The results from the reference standards should be compared with the known values and a judgment made concerning the completed analysis. If the results of the reference standards are equal to or within .+−. standard deviations of the known values, then the equipment, reagents and operations are performing satisfactorily.

Operation

Instrumental Set-Up
   1) Install the column in the gas chromatograph, and set up the instrumental conditions as in Table 1.
   2) Set up the data system with the appropriate method to acquire and analyze the data. The retention times may have to be adjusted in the method due to instrument variations. Consult the data system reference manual on how to do this—HP3350 User's Reference Manual. Unity response factors are used for each component.
   3) Obtain the shortening reference standard for analysis with the samples and ethylate it with the samples.

TABLE I

INSTRUMENTAL CONDITIONS

| | |
|---|---|
| Instrument | Hewlett-Packard 5890 |
| Column | 15 m .times. 0.25 mm I.D., coated with DB-WAX, 0.25 u film thickness |
| Column head pressure | 12.5 psi |
| Carrier gas | Helium |
| Injector "A" temperature | 210° C. |
| Split vent flow | 100 ml/min Septum purge 1.5 ml/min |
| Oven temperature profile: | |
| Initial temperature | 110° C. |
| Initial time | 1 min |
| Rate 1 | 15° C./min |
| Final temp 1 | 170° C. |
| Final time 1 | 0 min |
| Rate 2 | 6° C./min |
| Final temp 2 | 200° C. |
| Final time 2 | 0 min |
| Rate 3 | 10° C./min |
| Final temp 3 | 220° C. |
| Final time 3 | 8 min |
| Detector | FID |
| Detector temp | 230° C. |
| Make-up gas | 30 ml/min |
| Detector $C_2$ flow | 30 ml/min |
| Detector air flow | 300 ml/min |

Analysis of Samples—(The Samples are Analyzed with a Double Internal Standard.)

1) Dilute the reference mixture of FAME with hexane. The methyl esters should be approximately 2% in hexane. Inject one microliter of this solution via the autosampler. The results must meet the criteria in the Reference Standards section.
2) Prepare the triglyceride samples to be analyzed by adding two different internal standards, C9 and C21 triglycerides. C9 and C21 triglycerides are commercial standards consisting of 100% 9-carbon and 21-carbon triglycerides, respectively.) The internal standards are added to the samples at about 10% by weight of the sample. The samples (including the internal standards) are then converted to ethyl esters by any standard method.

3) Set up a sequence in the LAS data system to inject the samples.
4) Activate the autosampler to inject 1.0 microl. of the samples in the sequence. The gas chromatograph will automatically begin its temperature program and the data system will collect and analyze the data for the sequence.
5) The data is analyzed with the two internal standard procedure. The absolute amount (mg of esters per gram of sample) of the $C_6$ through C16 components is calculated from the C9 internal standard. The absolute amount of the $C_{18}$, C20, C22 and $C_{24}$ components is calculated from the C21 internal standard. Weight percentages of fatty acids are calculated from these amounts.

3. Ester Distribution of Polyol Polyesters

The relative distribution of the individual octa-, hepta-, hexa- and penta- esters, as well as collectively the tetra- through mono-esters, of the polyol polyesters can be determined using normal-phase high performance liquid chromatography (HPLC). A silica gel-packed column is used in this method to separate the polyester sample into the respective ester groupings noted above. Hexane and methyl-t-butyl ether are used as the mobile phase solvents. The ester groupings are quantitated using a mass detector (i.e., an evaporative light scattering detector). The detector response is measured and then normalized to 100%. The individual ester groups are expressed as a relative percentage.

4. Carbon Number Profile of Reduced Calorie Triglycerides

The carbon number profile (CNP) of the reduced calorie triglycerides is determined by programmed temperature gas chromatography (GC) using a short fused silica column coated with methyl silicone for analysis and characterization of the composition by molecular weight. The glycerides are separated according to their respective carbon numbers, wherein the carbon number defines the total number of carbon atoms on the combined fatty acid residues. The carbon atoms on the glycerol molecule are not counted. Glycerides with the same carbon number will elute as the same peak. For example, a triglyceride composed of three C16 (palmitic) fatty acid residues will co-elute with triglycerides made up on one C14 (myristic), one C16 and one $C_{18}$ (stearic) fatty acid residue or with a triglyceride composed of two C14 fatty acid residues and one C20 (arachidontc) fatty acid residue.

Preparation of the sample for analysis is as follows: 1.0 ml. of a tricaprin internal standard solution (2 microg./ml.) is pipetted into a vial. The methylene chloride solvent in the standard solution is evaporated using a steam bath under a nitrogen stream. Two drops of the sample (20 to 40 microg.) are pipetted into a vial. If the sample is solid, it is melted on a steam bath and stirred well to insure a representative sample. 1.0 ml. of bis (trimethylsilytrifluoroacetamide) (BSTFA) is pipetted into the vial which is then capped. The contents of the vial are shaken vigorously and then placed in a beating block (temperature of 100° C.) for about 5 minutes.

For determining the CNP/GC of the prepared samples, a Hewlett-Packard 5880A series gas chromatograph equipped with temperature programming and a hydrogen flame ionization detector is used together with a Hewlett-Packard 3351B data system. A 2 m. long, 0.22 mm. diameter fused silica capillary column coated with a thin layer of methyl silicone (Chrompak CP-SIL 5) is also used. The column is heated in an oven where temperature can be controlled and increased according to a specified pattern by the temperature programmer. The hydrogen flame ionization detector is attached to the outlet port of the column. The signal generated by the detector is amplified by an electrometer into a working input signal for the data system and recorder. The recorder prints out the gas chromatograph curve and the data system electronically integrates the area under the curve. The following instrument conditions are used with the gas chromatograph:

| | |
|---|---|
| Septum purge | 1 ml./min. |
| Inlet pressure | 5 lbs./in. sup.2 |
| Vent flow | 75 ml./min. |
| Makeup carrier | 30 ml./min. Hydrogen 30 ml./min |
| Air | 400 ml./min. |

1.0 microl. of the prepared sample is taken by a gas-tight syringe and injected into the sample port of the gas chromatograph. The components in the sample port are warmed up to a temperature of 365° C. and swept by a helium carrier gas to push the components into the column. The column temperature is initially set at 175° C. and held at this temperature for 0.5 min. The column is then heated up to a final temperature of 355° C. at a rate of 25° C./min. The column is maintained at the final temperature of 355° C. for an additional 2 min.

The chromatographic peaks, generated are then identified and the peak areas measured. Peak identification is accomplished by comparison to known pure glycerides previously programmed into the data system. The peak area as determined by the data system is used to calculate the percentage of glycerides having a particular Carbon Number ($C_N$) according to the following equation:

$$\% \ C_N = (\text{Area of } C_N/S) \times 100$$

wherein S=sum of Area of CN for all peaks generated.

The Area of CN is based upon the actual response generated by the chromatograph multiplied by a response factor for glycerides of the particular Carbon Number. These response factors are determined by comparing the actual responses of a mixture of pure glycerides of various Carbon Numbers to the known amounts of each glyceride in the mixture. A glyceride generating an actual response greater than its actual amount has a response factor less than 1.0; likewise, a glyceride generating a response less than that of its actual amount has a response factor of greater than 1.0. The mixture of glycerides used (in a methylene chloride solution) is as follows:

| Component | Carbon No. | Amount (mg./ml.) |
|---|---|---|
| Palmitic acid | 16 | 0.5 |
| Monopalmitin | 16 | 0.5 |
| Monostearin | 18 | 0.5 |
| Dipalmitin | 32 | 0.5 |
| Palmitostearin | 34 | 0.5 |
| Distearin | 36 | 0.5 |
| Tripalmitin | 48 | 1.5 |
| Dipalmiltostearin | 50 | 1.5 |

-continued

| Component | Carbon No. | Amount (mg./ml.) |
|---|---|---|
| Distearopalmitin | 52 | 1.5 |
| Tristearin | 54 | 1.5 |

5. Complete Melting Point of Polyol Polyesters by Differential Scanning Calorimetry (DSC)

As used herein, the term "complete melting point" refers to the temperature at which all solid components have melted. All melting points referred to herein are measured by Differential Scanning Calorimetry (DSC) as described below:

The complete melting point of the polyol polyester material or polyol polyester-containing particles used in this invention can be determined by DSC as follows:

Equipment:
Perkin-Elmer 7 Series Thermal Analysis System, Model DSC7, manufactured by Perkin-Elmer, Norwalk, Conn.

Procedure:
1. Sample of polyol polyester material or polyol polyester-containing blend is heated to at least 10° C. above the temperature at which all visible solids are melted and mixed thoroughly.
2. 10.+−.2 mg of sample is weighed into sample pan.
3. A scan is performed from about 10° C. above the temperature at which all visible solids are dissolved to −60° C. at 5° C. per minute.
4. The temperature of the sample is maintained at −60° C. for 3 minutes and scanned from 60° C. to the original starting temperature at 5° C. per minute (i.e., to about 10° C. above the temperature at which all visible solids are melted).
5. The complete melt point is the temperature at the intersection of the base line (i.e. specific heat line) with the line tangent to the trailing edge of the last (e.g., highest melting) endothermic peak.

Specific Illustrations of Reduced Calorie Fat Compositions Used in the Present Invention The following illustrates reduced calorie fat compositions and their use in various applications in accordance with the present invention:

A. Preparation of Polyol Polyesters and Reduced Calorie Triglycerides

1. Preparation of Liquid Sucrose Polyesters from Soybean Oil

Liquid sucrose polyesters are generally prepared from soybean oil (hydrogenated to Iodine Value 107) which is converted to the respective methyl esters and then reacted with sucrose in the presence of a potassium carbonate catalyst and the potassium soap of the soybean oil fatty acids. The resulting soybean oil polyesters have the fatty acid composition (FAC), and ester distribution (Esters) shown in the following table:

| FAC | % |
|---|---|
| C16:0 | 10.4 |
| C18:0 | 8.3 |

-continued

| | % |
|---|---|
| C18:1 | 45.8 |
| C18:2 | 32.8 |
| C18:3 | 2.1 |
| C20:0 | 0.2 |
| Other Esters | 0.4 |
| Octa | 90.5 |
| Hepta | 7.7 |
| Other | 1.8 |

2. Preparation of Liquid Sucrose Polyesters from Canola Oil

Liquid sucrose polyesters are prepared from canola oil (hydrogenated to Iodine Value 90) which is converted to the respective methyl esters and then reacted with sucrose in the presence of a potassium carbonate catalyst and the potassium soap of the canola oil fatty acids The resulting canola oil polyesters have the fatty acid composition (FAC) shown in the following table:

| FAC | % |
|---|---|
| C16:0 | 7.0 |
| C16:1 | 0.3 |
| C18:0 | 4.6 |
| C18:1 | 63.0 |
| C18:2 | 21.8 |
| C18:3 | 1.3 |
| C20:0 | 0.4 |
| C20:1 | 1.0 |
| C22:0 | 0.2 |
| C22:1 | 0.1 |
| Other | 0.4 |

3. Preparation of Viscous Sucrose Polyesters from Soybean Hardstock/Soybean Oil

Viscous sucrose polyesters are generally prepared from a 55:45 blend of soybean hardstock (hydrogenated to iodine value 8) and soybean oil (hydrogenated to iodine value 107) which is converted to the respective methyl esters and then reacted with sucrose in the presence of a potassium carbonate catalyst and the potassium soap of the soybean hardstock/soybean oil fatty acids. The resulting soybean hardstock/oil polyesters have the fatty acid composition (FAC), and ester distribution (Esters) shown in the following table:

| | % |
|---|---|
| FAC | |
| C16:0 | 9.6 |
| C18:0 | 52.7 |
| C18:1 | 21.3 |
| C18:2 | 14.7 |
| C18:3 | 1.0 |
| C20:0 | 0.5 |
| C22:0 | 0.2 |
| Esters | |
| Octa | 82.1 |
| Hepta | 17.9 |

4. Preparation of Solid Sucrose Polyesters from Myristic Acid

Solid sucrose polyesters are generally prepared from myristic acid (at least 99% pure) which is converted to the respective methyl esters and then reacted with sucrose in the presence of a potassium carbonate catalyst and the potassium soap of myristic acid. The resulting myristic acid polyesters have the fatty acid composition (FAC) and ester distribution (Esters) shown in the following table:

|  | % |
|---|---|
| FAC | |
| C12:0 | 0.2 |
| C14:0 | 99.3 |
| C16:0 | 0.1 |
| C18:0 | 0.2 |
| C18:1 | 0.2 |
| Esters | |
| Octa | 85.9 |
| Hepta | 12.8 |
| Hexa | 1.3 |

5. Preparation of Liquid Sucrose Polyesters from Palm Kernel Oil

Liquid sucrose polyesters are generally prepared from palm kernel oil (hydrogenated to an iodine value of about 4) which is converted to the respective methyl esters and then reacted with sucrose in the presence of a potassium carbonate catalyst and the potassium soap of the palm kernel oil fatty acids. The resulting palm kernel oil polyesters have the fatty acid composition (FAC) and ester distribution (Esters) shown in the following table:

|  | % |
|---|---|
| FAC | |
| C10:0 | 1.0 |
| C12:0 | 70.4 |
| C14:0 | 18.4 |
| C16:0 | 5.1 |
| C18:1 | 1.0 |
| C18:1 | 3.4 |
| C18:2 | 0.6 |
| Esters | |
| Octa | 85.9 |
| Hepta | 14.4 |
| Hexa | 1.0 |

6. Preparation of Behenic MCT's

The behenic MCT's (A or B) are generally prepared by random rearrangement (randomization) of tribehenin and medium chain triglycerides using sodium methoxide as the catalyst. The crude mixture resulting from randomization is then subjected to batch distillation (to remove a portion of the medium chain triglycerides), molecular distillation (to remove additional medium chain triglycerides and to separate the mono-long chain triglycerides from the di- and tri-long triglycerides) and nonsolvent fractional crystallization (to remove additional di-long chain triglycerides). The purified behenic MCT's obtained have the fatty acid composition (FAC) and carbon number profile (CNP) shown in the following table:

|  | A % | B % |
|---|---|---|
| FAC | | |
| C6:0 | 0.8 | 0.3 |
| C8:0 | 27.3 | 22.9 |
| C10:0 | 17.8 | 23.4 |
| C12:0 | 0.3 | 0.4 |
| C16:0 | 0.4 | 0.2 |
| C18:0 | 1.8 | 0.6 |
| C18:1 | 0.1 | 0.1 |
| C18:2 | — | 0.1 |
| C20:0 | 4.8 | 2.1 |
| C22:0 | 46.0 | 45.5 |
| C22:1 | 0.2 | 0.2 |
| C24:0 | 1.3 | 1.2 |
| CNP | | |
| 26 | 0.1 | |
| 28 | 0.6 | |
| 30 | 0.7 | |
| 32 | 1.3 | |
| 34 | 2.3 | 0.2 |
| 36 | 7.4 | 1.4 |
| 38 | 39.2 | 27.9 |
| 40 | 36.3 | 48.0 |
| 42 | 9.0 | 17.6 |
| 44 | 0.6 | 0.9 |
| 46 | 0.2 | 0.3 |
| 48 | 0.2 | 0.4 |
| 50 | 0.3 | 0.3 |
| 52 | 0.7 | 0.2 |
| 54 | 0.2 | 0.04 |

7. Preparation of Stearic/Behenic MCT's

The stearic/behenic MCTs are generally prepared by randomizing completely hydrogenated high erucic acid rapeseed oil with medium chain triglycerides using sodium methoxide as the catalyst, followed by batch distillation, molecular distillation and fractional crystallization of the crude mixture resulting from randomization. The purified stearic/behenic MCTs obtained have the fatty acid composition (FAC) and carbon number profile (CNP) shown in the following table:

|  | % |
|---|---|
| FAC | |
| C6:0 | 0.8 |
| C8:0 | 31.0 |
| C10:0 | 14.9 |
| C16:0 | 1.9 |
| C18:0 | 26.2 |
| C18:1 | 0.3 |
| C18:2 | 0.4 |
| C20:0 | 5.8 |
| C22:0 | 26.0 |
| C24:0 | 0.5 |
| CNP | |
| 26 | 0 |
| 28 | 0.5 |
| 30 | 0.7 |
| 32 | 3.2 |
| 34 | 24.0 |
| 36 | 26.4 |
| 38 | 27.8 |
| 40 | 12.2 |
| 42 | 2.0 |
| 44 | 1.0 |

| | % |
|---|---|
| 46 | 0.5 |
| 48 | 0.6 |
| 50 | 0.2 |

B. Clear Cooking and Salad Oils

Clear cooking and salad oils (at 70° F., 21.1 ° C.) are formulated from the above soybean oil polyesters, canola oil polyesters, behenic MCTs, stearic/behenic MCTs and soybean oil as follows:

| Component | % |
|---|---|
| CLEAR COOKING AND SALAD OIL I | |
| Soybean or canola oil polyesters | 25 |
| Behenic MCTs | 10 |
| Soybean oil | 65 |
| CLEAR COOKING AND SALAD OIL II | |
| Soybean or canola oil polyesters | 40 |
| Stearic/behenic MCTs | 20 |
| Soybean oil | 40 |
| CLEAR COOKING AND SALAD OIL III | |
| Soybean or canola oil polyesters | 70 |
| Behenic MCTs | 30 |
| CLEAR COOKING AND SALAD OIL IV | |
| Soybean or canola oil polyesters | 70 |
| Stearic/Behenic MCTs | 30 |
| CLEAR COOKING AND SALAD OIL V | |
| Soybean or canola oil polyesters | 50 |
| Behenic MCTs | 20 |
| Soybean Oil | 30 |

C. Frying Oils and Potato Clips

Frying oils for potato chips are formulated from the above soybean oil polyesters, soybean hardstock/oil polyesters, behenic MCTs and stearic/behenic MCTs as follows:

| Component | % |
|---|---|
| FRYING OIL I | |
| Soybean hardstock/oil polyesters | 22 |
| Soybean oil polyesters | 28 |
| Stearic/behenic MCTs | 43 |
| Behenic MCTs (A) | 7 |
| FRYING OIL II | |
| Soybean oil polyesters | 70 |
| Behenic MCTs (A) | 30 |
| FRYING OIL III | |
| Soybean oil polyesters | 85 |
| Behenic MCTs (A) | 15 |
| FRYING OIL IV | |
| Soybean oil polyesters | 85 |
| High $C_{20}$ and above long-chain fatty acid polyesters (from U.S. Pat. No. 5,306,514) | 5 |

Ninety grams of sliced potatoes are fried in 11 kg. of frying oil I, II, III, or IV at a temperature of 365° F. (185° C.) for 3 minutes, 5 seconds, to provide potato chips.

D. Chocolate-Flavored Candy Bar

A blend containing the myristic acid polyesters is prepared from the following ingredients:

| Ingredient | Grams |
|---|---|
| Chocolate liquor | 3.6 |
| Cocoa powder (11% cocoa butter) | 5.1 |
| Sweet cream powder (72% milkfat) | 2.4 |
| Lecithin | 0.1 |
| Natural/artificial butter flavors | 0.14 |
| Sucrose powder (extra fine) | 15.7 |
| Myristic acid polyester | 14.0 |

The above blend is heated to, 135° F. (57.2° C.) in a glass beaker and then gradually cooled to 90° F. (32.2° C.) with mixing until the blend becomes smooth and lump-free.

A blend containing the behenic MCT's is prepared from the following ingredients:

| Ingredient | Grams |
|---|---|
| Behenic MCT's (B) | 14.0 |
| Soybean lecithin | 0.12 |
| Cocoa powder (11% cocoa butter) | 7.7 |
| Nonfat milk solids | 9.0 |
| Vanilla flavor | 0.18 |
| Sucrose | 28.0 |

The above blend is passed twice through a 4-roll mill to reduce the particle size of the sucrose. The roll milled behenic MCT-containing blend is then combined with the myristic acid polyester-containing blend, poured at 90° F. (32.2° C.) into chocolate bar molds, cooled at 50° F. (10° C.) for 48 hours and then gradually warmed to 70° F. (21.1° C.) in a styrofoam cooler. The tempered chocolate-flavored candy bars are then demolded.

E. Margarine-Like Spread

The aqueous phase of the margarine-like spread is formulated from the following ingredients:

| Ingredient | Grams |
|---|---|
| Water | 150 |
| Distilled mono- and diglycerides | 1.5 |
| Lecithin | 1.0 |
| Natural/artificial butter flavors | 0.09 |
| Salt | 11.0 |
| Potassium Sorbate | 0.12 |
| Citric acid | 0.04 |

The above aqueous phase ingredients are dissolved in the water and then heated to 130° F. (54.4° C.).

The fat phase of the margarine-like spread is formulated from the following ingredients:

| Ingredient | Grams |
| --- | --- |
| Stearic/behenic MCT's | 290.7 |
| Palm kernel oil polyesters | 180.0 |
| Soybean hardstock/oil polyesters | 180.0 |
| Soybean oil polyesters | 180.0 |

The aqueous phase ingredients are blended into the fat phase ingredients at 130° F. (54.4° C.) under high shear mixing conditions using an Agi mixer equipped with a homogenizer head, a rotating bowl and Teflon scrapper blades to remove emulsified and crystallized material from the inside wall of the bowl. Chilled water is sprayed on the outside wall of the bowl to cool it. As the mass in the bowl is cooled to approximately 67° F. (19.4° C.), the viscosity increases to that of a typical soft margarine consistency. The emulsified/crystalized material is filled into plastic tubs, placed in a 32° F. (0° C.) bath for 1 hour and then stored for 48 hours in a 40° F. (4.4° C.) constant temperature room to provide a soft, spreadable margarine-like product.

F. Frozen Strawberry-Flavored Dessert

A frozen strawberry-flavored dessert is formulated from the following ingredients:

| Ingredient | Grams |
| --- | --- |
| Frozen strawberries (thawed and homogenized) | 700 |
| Palm kernel oil polyesters | 208 |
| Stearic/behenic MCT's | 112 |
| Polyglycerol ester emulsifier | 18 |
| Propylene glycol monostearate | 8 |
| Dariloid (gum mixture) | 4 |
| Sucrose | 320 |
| Vanilla extract | 4 |
| Dried cream extract | 10 |
| Skim milk | 569 |
| Artificial cream flavors | 2 |

Except for the strawberries, the above ingredients are homogenized at 120.degree.–135° F. (48.9.degree.–57.2° C.) for about 10 minutes under high shear mixing using the same equipment as in the margarine-like spread example, but with chilled propylene glycol as the coolant. This homogenized mixture is cooled to 63° F. (17.2° C.) and then a portion (approximately 500 g.) of the strawberries are added. This homogenized mixture is cooled further to 40° F. (4.4° C.) and then the remaining portion of the strawberries are added. After further cooling, this mixture starts to freeze at 30° F. (−1.1° C.). After freezing begins, this mixture is cooled for about 10 additional minutes before being transferred into one-pint containers. This entire cooling/freezing process takes place in about 30 minutes. The pint containers are stored for 2 to 3 hours at approximately −40° F. (−40° C.) to provide the final ice cream-like frozen strawberry-flavored dessert.

What is claimed:

1. A reduced calorie fat composition which comprises:
   a. from about 70% to about 80% of an edible, substantially nonabsorbable, substantially nondigestible polyol fatty acid polyester which has a melting point less than or equal to 37° C., and has at least 4 fatty acid ester groups, wherein each fatty acid group has from 8 to 22 carbon atoms, and wherein the fatty acid groups in said polyol polyester are formed predominantly from the fatty acids of oleic acid, linoleic acid and mixtures thereof; and
   b. from about 20% to about 30% reduced calorie triglycerides selected from MMM, MLM, MML, LLM, LML and LLL triglycerides, and mixtures thereof; wherein M is a saturated fatty acid residue selected from (26 to $C_6$ to $C_{10}$ saturated fatty acids, and mixtures thereof; wherein L is a saturated fatty acid residue selected from $C_{18}$ to $C_{24}$ saturated fatty acids and mixtures thereof; wherein the reduced calorie triglycerides comprise: (1) at least about 90% combined MLM, MML, LLM and LML triglycerides; (2) up to about 10% combined MMM and LLL triglycerides, and wherein the fatty acid composition of the reduced calorie triglycerides comprises: (1) from about 20% to about 65% $C_6$ to $C_{10}$ saturated fatty acids; (2) from about 40% to about 80% $C_{18}$ to $C_{24}$ saturated fatty acids; and (3) from about 30% to about 70% $C_{20}$ to $C_{24}$ saturated fatty acids.

2. A fat-containing, chocolate-flavored food product having fat ingredients and nonfat ingredients wherein from about 10 to 100% of the total fat comprises a reduced calorie fat composition comprising:
   a. from about 65% to about 80% of a solid sucrose octaester having $C_{12}$ to $C_{14}$ fatty acid groups; and
   b. from about 20% to about 35% reduced calorie triglycerides selected from MMM, MLM, MML, LLM, LML and LLL triglycerides, and mixtures thereof; wherein M is a saturated fatty acid residue selected from $C_6$ to $C_{10}$ saturated fatty acids, and mixtures thereof; wherein L is a saturated fatty acid residue selected from $C_{18}$ to $C_{24}$ saturated fatty acids and mixtures thereof; wherein the reduced calorie triglycerides comprise: (1) at least about 85% combined MLM, MML, LLM and LML triglycerides; (2) up to about 15% combined MMM and LLL triglycerides, and wherein the fatty acid composition of the reduced calorie triglycerides comprises: (1) from about 10% to about 70% $C_6$ to $C_{10}$ saturated fatty acids; (2) from about 30% to about 90% $C_{18}$ to $C_{24}$ saturated fatty acids; and (3) from about 20% to about 80% $C_{20}$ to $C_{24}$ saturated fatty acids.

3. The chocolate-flavored product of claim 2 wherein the reduced calorie fat composition comprises from about 65% to about 80% of a sucrose octaester having at least about 90% myristic acid groups and from about 20% to about 35% of said reduced calorie triglycerides having at least about 80% $C_{38}$ to $C_{42}$ triglycerides, from about 30% to about 50% $C_8$ to $C_{10}$ saturated fatty acids and from about 40% to about 60% behenic acid.

4. A reduced calorie fat composition which comprises:
   a. from about 65% to about 80% of an edible, substantially nonabsorbable, substantially non-digestible polyol fatty acid polyester which comprises at least 3% of a solid non-digestible polyol polyester component having a melting point of greater than 37° C., having at least 4 fatty acid ester groups; wherein the polyol is selected from sugars and sugar alcohols containing from 4 to 8 hydroxy groups; and wherein each fatty acid group has from 2 to 24 carbon atoms, and further wherein the fatty acid groups in said polyol polyester are formed predominantly from the fatty acids of oleic acid, linoleic acid and mixtures thereof; and
   b. from about 20% to about 35% reduced calorie triglycerides selected from MMM, MLM, MML, LLM, LML and LLL triglycerides, and mixtures thereof; wherein M is a saturated fatty acid residue selected from $C_6$ to $C_{10}$ saturated fatty acids, and mixtures thereof; wherein L is a saturated fatty acid residue selected from $C_{18}$ to $C_{24}$ saturated fatty acids, and mixtures thereof; wherein the reduced calorie triglycerides comprise: (1) at least about 90% combined MLM, MML, LLM and LML triglycerides; (2) up to about 10% combined MMM and LLL triglycerides, and wherein the fatty acid composition of the reduced calorie triglycerides comprises: (1) from about 20% to about 65% $C_6$ to $C_{10}$ saturated fatty acids; (2) from about 40% to about 80% $C_{18}$ to $C_{24}$ saturated fatty acids; and (3) from about 20% to about 80% $C_{20}$ to $C_{24}$ saturated fatty acids.

* * * * *

UNITED STATES PATENT AND TRADEMARK OFFICE
CERTIFICATE OF CORRECTION

PATENT NO.        : 7,241,468 B2
APPLICATION NO.   : 10/149875
DATED             : July 10, 2007
INVENTOR(S)       : Russell Bruce Naber It is certified that error appears in the above-identified patent and that said Letters Patent is hereby corrected as shown below:

Column 34, Line 8, omit "M is a saturated fatty acid residue selected from (26 to $C_6$ to $C_{10}$ saturated fatty acids and mixtures thereof;" and insert --M is a saturated fatty acid residue selected from $C_6$ to $C_{10}$ saturated fatty acids and mixtures thereof;--

Signed and Sealed this

Twenty-seventh Day of May, 2008

JON W. DUDAS
*Director of the United States Patent and Trademark Office*